US006169103B1

(12) United States Patent
Purchase, Jr. et al.

(10) Patent No.: US 6,169,103 B1
(45) Date of Patent: *Jan. 2, 2001

(54) FLUORINE-SUBSTITUTED BIPHENYL BUTYRIC ACIDS AND THEIR DERIVATIVES AS INHIBITORS OF MATRIX METALLOPROTEINASES

(75) Inventors: Claude Forsey Purchase, Jr., Ann Arbor; Bruce David Roth, Plymouth; Gerald Paul Schielke; Lary Craswell Walker, both of Ann Arbor; Andrew David White, Pinckney, all of MI (US)

(73) Assignee: Warner-Lambert, Morris Plains, NJ (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/256,714

(22) Filed: Feb. 24, 1999

Related U.S. Application Data
(60) Provisional application No. 60/076,633, filed on Mar. 3, 1998.

(51) Int. Cl.$^7$ .................. A61K 31/40; A61K 31/275; C07D 209/48

(52) U.S. Cl. .................. 514/389; 514/389; 514/522; 514/419; 514/567; 558/414; 548/494; 548/319.5; 548/477; 560/35; 562/492

(58) Field of Search .................. 558/414; 548/319.5, 548/494, 477, 479; 562/440; 560/35; 514/425, 522, 555, 389, 419, 417, 567

(56) References Cited

FOREIGN PATENT DOCUMENTS

WO 97145402  12/1997  (WO).
98 09940     3/1998   (WO).

OTHER PUBLICATIONS

Aisen, P. S., "Antiflammatory therapy for Alzheimer's disease," *Dementia,*1995;9:173–182.

Andersen, K., Launer, L. J., Ott A., Hoes A. W., Breteler M.M.B., and Hofman A., "Do nonsteroidal anti–inflammatory drugs decrease the risk for Alzheimer's disease?"The Rotterdam Study, *Neurology*1995;45:1441–45.

Andrews H. J., Plumpton T. A., Harper G. P., and Cawston T. E., "A synthetic peptide metalloproteinase inhibitor, but not Timp, prevents the breakdown of proteoglycan within articular cartilage in vitro", *Agents Actions*, 1992;37:145–154.

Armstrong P. W., Moe G. W., Howard R. J., Grima E. A., and Cruz T. F., "Structural remodeling in heart failure: Gelatinase induction,", *Can. J. Cardiol.*, 1994;10:214–220.

Bagchus W. M., Hoedemaeker P. J., Rozing J., Bakker W. W., "Glomerulonephritis induced by monoclonal anti–Thy 1.1 antibodies: A sequential histological and ultrastructural study in the rat", *Lab. Invest.*, 1986;55:680–687.

Bendeck M. P., Zemp N., Clowes A. W., Galardy R. E., and Reidy M., "Smooth muscle cell migration and matrix metalloproteinase expression after arterial injury in the rat," *Circulation Research*, 1994;75:539–545.

Benelli R., Adatia R., Ensoli B., Stetler–Stevenson W.G., Santi L., and Albini A., "Inhibition of AIDS—Kaposi's sarcoma cell induced endothelial cell invasion by TIMP–2 and a synthetic peptide from the metalloproteinase propeptide: Implications for an anti–angiogenic therapy", *Oncology Research*, 1994;6:251–257.

Berge S.M. et al., "Pharmaceutical Salts," *J. of Pharma. Sci.*, 1977;66:1–19.

Breitner J.C.S., Gau B.A., Welsh K.A., et al., "Inverse association of anti–inflammatory treatments and Alzheimer's disease: Initial results of a co–twin control study," *Neurology*, 1994;44:227–32.

Breitner J.C.S., Welsh K.A., Helms M.J., et al., "Delayed onset of Alzheimer's disease with nonsteroidal anti–inflammatory and histamine H2 blocking drugs," *Neurobiol. Aging*, 1995;16:523–30.

Brown P.D., Levy A.T., Margulies I., Liotta L.A., Stetler–Stevenson W.G., "Independent expression and cellular processing of M,72,000 type IV collagenase and interstitial collagenase in human tumorigenic cell lines," *Cancer Res.*, 1990;50:6184–6191.

Brown S.I., Weller C.A., and Wasserman H.E., "Collagenolytic activity of alkali–burned corneas," *Arch. Ophthalmol.*, 1969;81:370–373.

Burns F.R., Stack M.S., Gray R.D., and Paterson C.A., "Inhibition of Purified collagenase from Alkali–burned rabbit corneas", *Invest. Ophthalmol,*, 1989;30:1569–1575.

Chang Y. et al., "Adjuvant Polyarthritis, IV. Induction by a Synthetic Adjuvant: Immunologic, Histopathologic, and Other Studies," *Arthritis and Rheumatism*, vol. 23, No. 1, pp. 62–71 (Jan. 1980).

(List continued on next page.)

Primary Examiner—Cecilia Tsang
Assistant Examiner—Ebenezer Sackey
(74) *Attorney, Agent, or Firm*—Merchant & Gould P.C.

(57) ABSTRACT

Fluorine-substituted biphenyl butyric acid compounds and derivatives are described as well as acid methods for the preparation and pharmaceutical compositions of same, which are useful as inhibitors of matrix metalloproteinases, particularly gelatinase A, stromelysin-1, and collagenase-3, and for the treatment of atherosclerotic plaque rupture, aortic aneurism, heart failure, restenosis, periodontal disease, corneal ulceration, treatment of burns, decubital ulcers, wound healing, cancer, inflammation, pain, arthritis, osteoporosis, multiple sclerosis, renal disease, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

29 Claims, No Drawings

OTHER PUBLICATIONS

Clark R.K., Lee E.V., Fish C.J., et al., "Development of tissue damage, inflammation and resolution following stroke: an immunohistochemical and quantitative planimetric study," *Brain Res. Bull.*, 1993:31:565–72.

Davies et al., "A synthetic matrix metalloproteinase inhibitor decreases tumor burden and prolongs survival of mice bearing human ovarian carcinoma xenografts", *Cancer Res.*, 1993;53:2087–2091.

Davies M. et al., "Proteinases and glomerular matrix turnover," *Kidney Int.*, 1992;41:671–678.

DeClerck Y.A. et al., "Inhibition of Invasion and Metastasis in Cells Transfected with an Inhibitor of Metalloproteinases," *Cancer Research*, vol. 52, pp. 701–708 (Feb. 1, 1992).

Freiji J.M., Diez–Itza I., Balbin M., Sanchez L.M., Blasco R., Tolivia J., and Lopez–Oitn C., "Molecular cloning and expression of collagenase–3, a novel human matrix metalloproteinase produced by breast carcinomas", *J. Biol. Chem.*, 1994;269:16766–16773.

Ellis A.J., Curry V.A., Powell E.K., and Cawston T.E., "The prevention of collagen breakdown in bovine nasal cartilage by TIMP, TIMP–2 and a low molecular weight synthetic inhibitor", *Biochem. Biophys. Res. Commun.*, 1994;201:94–101.

Galis Z.S., Sukhova G.K., Lark M.W., and Libby P., "Increased expression of matrix metalloproteinases and matrix degrading activity in vulnerable regions of human atherosclerotic plaques," *J. Clin. Invest.*, 1994;94:2493–2503.

Gendelman H.E. and Tardieu M., "Macrophages/microglia and the pathophysiology of CNS injuries in AIDS," *J. Leukocyte Biol.*, 1994;56:387–8.

Gijbels et al., "Reversal of experimental autoimmune encephalomyelitis with a hydroxamate inhibitor of matrix metalloproteases", *J, Clin. Invest.*1994;94:2177–2182.

Giulian D. And Vaca K., "Inflammatory glia mediate delayed neuronal damage after ischemia in the central nervous system," *Stroke*, 1993;24(Suppl 12):184–90.

Grams F. et al., "X–ray structures of human neutrophil collagenase complexed with peptide hydroxyamate and thiol inhibitors. Implications for substrate binding and rational drug design," *Eur. J. Biochem.*, 1995;228:830–841.

Hampel H. And Müller N., "Inflammatory and immunological mechanisms in Alzheimer's disease," *DN&P*, 1995;8:599–608.

Henney A.M., Wakeley P.R., Davies M.J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158.

Kitamura M. et al., "Gene transfer of metalloproteinase transin induces aberrant behavior of cultured mesangial cells," *Kidney Int.*, 1994;45:1580–1586.

Lee T.H., Hamilton M.A., Stevenson L.W., Moroguchi J.D., Fonarow G.C., Child J.S., Lakes H., and Walden J.A., "Impact of left ventricular size on the survival in advanced heart failure," *Am. J. Cardiol.*, 1993;72:672–676.

Leigh P.N., "Pathogenic mechanisms in amyotrophic lateral sclerosis and other motor neuron disorders". In: Calne D.B., ed., Neurodegenerative Diseases, W.B. Saunders Company, 1994:473–88.

Lovett D.H., Johnson R.J., Marti H.P., Martin J., Davies M., Couser W.G., "Structures characterization of the mesangial cell type IV collagenase and enhanced expression in a model of immune complex mediated glomerulonephritis," *Am. J. Pathol.*, 1992;141:85–98.

Lucca U., Tettamanti M., Forloni G., and Spagnoli A., "Nonsteroidal anti–inflammatory drug use in Alzheimer's disease," *Biol. Psychiatry*, 1994;36;854–66.

Mandybur T.I. and Balko G., "Cerebral amyloid angiopathy with granulomatous angiitis ameliorated by steroid–cytoxan treatment," *Clin. Neuropharm.*, 1992;15:241–7.

Marti H.P. et al., "Homology cloning of rat 72 kDa type IV collagenase: Cytokine and second–messenger inducibility in mesangial cells," *Biochem. J.*, 1993;291:441–446.

Marti H.P. et al., "Transforming growth factor–$\beta$1 stimulates glomerular mesangial cell synthesis of the 72 kDa type IV collagenase," *Am. J. Pathol.*, 1994;144:82–94.

Martin J. et al., "Enhancement of glomerular mesangial cell neutral proteinase secretion by macrophages: role of interleukin $1^1$," *J. Immunol.*, 1986;137:525–529.

Martin R. and McFarland H.F., "Immunological aspects of experimental allergic encephalomyelitis and multiple sclerosis," *Crit. Rev. Clin. Lab. Sci.*, 1995;32:121–82.

Martin R., MacFarland H.F., and McFarlin D.E., "Immunological aspects of demyelinating diseases[1]," *Annul Rev. Immunol.*, 1992;10:153–87.

McGeer E.G. and McGeer P.L., "Neurodegeneration and the immune system". In: Calne D.B., ed. Neurodegenerative Diseases, W.B. Saunders Company, 1994:277–299.

McGeer P.L., Rogers J., and McGeer E.G., "Neuroimmune mechanisms in Alzheimer disease pathogenesis," *Alzheimer Dis. Assoc. Disorders*, 1994;8:149–58.

McGeer P.L. and Rogers J., "Anti–inflammatory agents as a therapeutic approach to Alzheimer's disease," *Neurology*, 1992;42:447–9.

Melchiori A., Albili A., Ray J.M., and Stetler–Stevenson W.G., "Inhibition of tumor cell invasion by a highly conserved peptide sequence from the matrix metalloproteinase enzyme prosegment", *Cancer Res.*, 1992;52:2353–2356.

Monsky W.L., Kelly T., Lin C.–Y., Yeh Y., Stetler–Stevenson W.G., Meuller S.C., and Chen W.–T., "Binding and localization of $M_r$ 72,000 matrix metallopriteinase at cell surface invadopodia", *Cancer Res.*, 1993;53:3159–3164.

Overall C.M., Wiebkin O.W., and Thonard J.C., "Demonstration of tissue collagenase activity in vivo and its relationship to inflammation severity in human gingiva," *J. Periodontal Res.*1987;22:81–88.

Patterson P.H., "Cytokines in Alzheimer's disease and multiple sclerosis," *Cur. Opinion Neurobiol.*, 1995;5:642–646.

Pauly R.R., Passaniti A., Bilato C., Monticone R., Cheng L., Papadopoulos N., Gluzband Y.A., Smith L., Weinstein C., Lakatta E., and Crow M.T., "Migration of cultured vascular smooth muscle cells through a basement membrane barrier requires typr IV collagenase activity and is inhibited by cellular differentiation," *Circulation Research*, 1994;75:41–54.

Romanic A.M., and Madri J.A., "The Induction of 72–kDa Gelatinase in T Cells upon Adhesion to Endothelial Cells is VCAM–1 Dependent," *J. Cell Biology*, 1994;125:1165–1178.

Reddy H.K., Tyagi S.C., Tjaha I.E., Voelker D.J., Campbell S.E., and Weber K.T., "Activated myocardial collagenase in idiopathic dilated cardiomyopathy: a marker of dilation and remodeling," *Clin. Res.*, 1993;41:660A.

Rich J.B., Rasmusson D.X., Folstein M.F., et al., "Nonsteroidal anti–inflammatory drugs in Alzheimer's disease," *Neurology*, 1995;45:51–5.

Rogers J., Webster S., Lue L.F., et al., "Inflammation and Alzheimer's disease pathogenesis", In:*Neurobiology og Aging*, 1996;17:681–686.

Rothwell N.J. and Relton J.K., "Involvement of cytokines in acute neurodegeneration in the CNS," *Neurosci. Biobehav. Rev.*, 1993l17:217–27.

Saarialho–Kere U.K., Ulpu K., Pentland A.P., Birkedal–Hansen H., Parks W.C., and Welgus H.G., "Distinct Populations of Basal Keratinocytes Express Stromelysin–1 ans Stromelysin–2 in Chronic Wounds," *J. Clin. Invest.*, 1994;94:79–88.

Sabbah H.N., Kono T., Stein P.D., Mancini G.B., and Goldstein S., "Left ventricular shape changes during the course of evolving heart failure," *Am. J. Physiol.*, 1992;263:H266–270.

Sato H., Takino T., Okada Y., Cao J., Shinagawa A., Yamamoto E., and Seiki M., "A matrix metalloproteinase expressed on the surface of invasive tumour cells", *Nature*, 1994;370:61–65.

Strongin A. Y., Marmer B.L., Grant G.A., and Goldberg G.I., "Plasma membrane–dependent Activation of the 72–kDa type IV collagenase is prevented by complex formation with TIMP–2", *J. Biol. Chem.*, 1993;268:14033–14039.

Taraboletti G., Garofalo A., Belotti D., Drudis T., Borsotti P., Scanziani E., Brown P.D., and Giavazzi R., "Inhibtion of angiogenesis and murine hemangioma growth by batimastat, a synthetic inhibitor of matrix metalloproteinases", *Journal of the National Cancer Institute*, 1995;87:293.

Turck J. et al., "Matrix metalloproteinase 2 (gelatinase A) regulates glomerular cell proliferation and differentiation," *J. Biol. Chem.*, 1996;271:15074–15083.

Tyagi S.C., Reddy H.K., Voelker D., Tjara I.E., and Weber K.T., "Myocardial collagenase in failing human heart," *Clin. Res.*, 1993;41:681A.

Uitto V.J., Applegren R., and Robinson P.J., "Collagenase and neutral metallo–proteinase activity in extracts from inflamed human gingiva," *J. Periodontal Res.*, 1981;16:417–424.

Vincenti M.P. et al., "Using inhibitors of metalloproteinases to treat athritis," *Athritis Rheum.*, 1994;37:8:1115–1126.

Vine N. And Powell J.T., "Metalloproteinases in degenerative aortic diseases," *Clin.Sci.*, 1991;81:233–239.

Walakovits L.A., Moore V.L., Bhardwaj N., Gallick G.S., and Lark M.W., Detection of stromelysin and collagenase in synovial fluid from patients with rheumatoid athritis and post–traumatic knee injury,*Athritis Rheum.*, 1992;35:35–42.

Woessner J.F., "Matrix metalloproteinases and their inhibitors in connective tissue remodeling," *FASEB J.*, 1991;5:2145–2154.

Ye Q.–Z., Johnson L.L., Hupe D.J., and Baragi V., "Purification and Characterization of the Human Stromelysin Catalytic Domain Expressed in *Escherichia coli*," *Biochemistry*, 1992;31:11231–11235.

Zafarullah M., Pelletier J.P., Cloutier J.M., and Marcel–Pelletier J., "Elevated metalloproteinases and tissue inhibitor of metalloproteinase mRNA in human osteoarthritic synovia," *J. Rheumatol.*, 1993;20:693–697.

FLUORINE-SUBSTITUTED BIPHENYL BUTYRIC ACIDS AND THEIR DERIVATIVES AS INHIBITORS OF MATRIX METALLOPROTEINASES

This application claims benefit of provisional application Ser. No. 60/076,633 filed Mar. 3, 1998.

BACKGROUND OF THE INVENTION

The present invention relates to novel fluorine-substituted biphenyl butyric acid compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (MMP-2), stromelysin-1 (MMP-3), and collagenase (MMP-13). More particularly, the novel compounds of the present invention are useful in the treatment of atherosclerotic plaque rupture, aortic aneurism, heart failure, restenosis, periodontal disease, corneal ulceration, treatment of burns, decubital ulcers, wound repair, cancer, inflammation, pain, arthritis, osteoporosis, multiple sclerosis, renal disease, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154). Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994;269:16766–16773), and the membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques", *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization", *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases", *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure", *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy", *Clin. Res.*, 1993;41:660A; Tyagi S. C., Reddy H. K., Voelker D., Tjara I. E., and Weber K. T., "Myocardial collagenase in failing human heart", *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction", *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure", *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat", *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T. "Migration of cultured vascular smooth muscle cells through a basement membrane barrier requires type IV collagenase activity and is inhibited by cellular differentiation", *Circulation Research*, 1994;75:41–54).

Collagenase and stromelysin activities have been demonstrated in fibroblasts isolated from inflamed gingiva (Uitto V.

J., Applegren R., and Robinson P. J., "Collagenase and neutral metalloproteinase activity in extracts from inflamed human gingiva", *J. Periodontal Res.*, 1981;16:417424), and enzyme levels have been correlated to the severity of gum disease (Overall C. M., Wiebkin O. W., and Thonard J. C., "Demonstrations of tissue collagenase activity in vivo and its relationship to inflammation severity in human gingiva", *J. Periodontal Res.*, 1987;22:81–88). Proteolytic degradation of extracellular matrix has been observed in corneal ulceration following alkali burns (Brown S. I., Weller C. A., and Wasserman H. E., "Collagenolytic activity of alkali burned corneas", *Arch. Ophthalmol.*, 1969;81 :370–373). Thiol-containing peptides inhibit the collagenase isolated from alkali-burned rabbit corneas (Burns F. R., Stack M. S., Gray R. D., and Paterson C. A., *Invest. Ophthalmol.*, 1989;30: 1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds", *J. Clin. Invest.*, 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies, et al., (*Cancer Res.*, 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.*, 1992;52:2353–2356). The natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.*, 1992;52:701–708). Studies of human cancers have shown that gelatinase A is activated on the invasive tumor cell surface (Strongin A. Y., Marmer B. L., Grant G. A., and Goldberg G. I., *J. Biol. Chem.*, 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.*, 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute*, 1995;87:293 and Benelli R., Adatia R., Ensoli B., Stetler-Stevenson W. G., Santi L., and Albini A, *Oncology Research*, 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury", *Arthritis Rheum.*, 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia", *J. Rheumatol.*, 1993;20:693–697). TIMP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions*, 1992;37:147–154; Ellis A. J., Curry V. A., Powell E. K., and Cawston T. E., *Biochem. Biophys. Res. Commun.*, 1994;201 :94–101).

Gijbels, et al., (*J. Clin. Invest.*, 1994;94:2177–2182) recently described a peptide hydroxamate, GM600 1, that suppressed the development or reversed the clinical expression of experimental autoimmune encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent", *J. Cell Biology*, 1994; 125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G., and McGeer P. L., "Neurodegeneration and the immune system", In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders", In: Calne D. B., ed., Neurodegenerative Diseases, W. B. Saunders, 1994:473–88), cerebral amyloid angiopathy (Mandybur T. I. and Balko G., "Cerebral amyloid angiopathy with granulomatous angiitis ameliorated by steroid-cytoxan treatment", *Clin. Neuropharm.*, 1992;15:241–7), AIDS (Gendelman H. E. and Tardieu M., "Macrophages/microglia and the pathophysiology of CNS injuries in AIDS", *J. Leukocyte Biol.*, 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases", *Annul Rev. Immunol.*, 1992;10:153–87; Clark R. K., Lee E. V., Fish C. J., et al., "Development of tissue damage, inflammation and resolution following stroke: an immunohistochemical and quantitative planimetric study", *Brain Res. Bull.,* 1993;31:565–72; Giulian D. and Vaca K., "Inflammatory glia mediate delayed neuronal damage after ischemia in the central nervous system", *Stroke,* 1993;24(Suppl 12):184–90; Patterson P. H., "Cytokines in Alzheimer's disease and multiple sclerosis", *Cur. Opinion Neurobiol.,* 1995;5:642–6; McGeer P. L., Rogers J., and McGeer E. G., "Neuroimmune mechanisms in Alzheimer disease pathogenesis", *Alzheimer Dis. Assoc. Disorders,* 1994;8:149–58; Martin R. and McFarland H. F., "Immunological aspects of experimental allergic encephalomyelitis and multiple sclerosis", *Crit. Rev. Clin. Lab. Sci.,* 1995;32:121–82; Rogers J., Webster S., Lue L. F., et al., "Inflammation and Alzheimer's disease pathogenesis", In: *Neurobiology of Aging,* 1996;17:681–686; Rothwell N. J. and Relton J. K., "Involvement of cytokines in acute neurodegeneration in the CNS", *Neurosci. Biobehav. Rev.,* 1993; 17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer, et al., supra., 1994; Rogers, et al., supra.); 2) There is evidence that β-amyloid induces neurodegenerative changes primarily through interactions with inflammatory molecules, and that inflammation alone is sufficient to induce neurodegeneration (Rogers et al., supra); and 3) Growing epidemiological data indicate that antiinflammatory therapy can delay the onset and slow the progression of Alzheimer's disease (McGeer P. L. and Rogers J., "Anti-inflammatory agents as a therapeutic approach to Alzheimer's disease", *Neurology,* 1992;42:447–9; Canadian Study of Health and Aging, "Risk factors for Alzheimer's disease in Canada", *Neurology,* 1994;44:2073–80; Lucca U., Tettamanti M., Forloni G., and Spagnoli A., "Nonsteroidal antiinflammatory drug use in Alzheimer's disease", *Biol. Psychiatry,* 1994;36:854–66; Hampel H. and Müller N., "Inflammatory and immunological mechanisms in Alzheimer's disease", *DN&P,* 1995;8:599–608; Breitner J. C. S., Gau B. A., Welsh K. A., et al., "Inverse association of anti-inflammatory treatments and Alzheimer's disease: Initial results of a co-twin control study", *Neurology,* 1994;44:227–32; Breitner J. C. S., Welsh K. A., Helms M. J., et al., "Delayed onset of Alzheimer's disease with nonsteroidal anti-inflammatory and histamine H2 blocking drugs", *Neurobiol. Aging,* 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease? The Rotterdam Study", *Neurology,* 1995;45:1441–5; Rich J. B., Rasmusson D. X., Folstein M. F., et al., "Nonsteroidal anti-inflammatory drugs in Alzheimer's disease", *Neurology,* 1995;45:51–5; Aisen P. S., "Anti-inflammatory therapy for Alzheimer's disease", *Dementia,* 1995;9: 173–82; Rogers, et al., supra). Chronic use of nonsteroidal antiinflammatory drugs (NSAIDs), most commonly for the treatment of rheumatoid arthritis, decreases the probability of developing Alzheimer's disease, and there is reason to believe that other antiinflammatory agents may also be effective, although direct evidence for the efficacy of such treatments is lacking (Hamper and Müller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as antiinflammatory/immuno-suppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An antiinflammatory drug that is well-tolerated by patients and that crosses the blood-brain barrier has significant advantages for the treatment of acute and chronic degenerative diseases of the central nervous system.

Normal kidney function is dependent on the maintenance of tissues constructed from differentiated and highly specialized renal cells which are in a dynamic balance with their surrounding extracellular matrix (ECM) components (Davies M., et al., "Proteinases and glomerular matrix turnover," *Kidney Int.,* 1992;41 :671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). The MMP belong to a supergene family of zinc endopeptidases (Woessner J. F., "Matrix metalloproteinases and their inhibitors in connective tissue remodelling," *FASEB J.,* 1991;5:2145–2154). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can upregulate metalloproteinase expression in renal mesangial cells (Martin J., et al., "Enhancement of glomerular mesangial cell neutral proteinase secretion by macrophages: role of interleukin 1," *J. Immunol.,* 1986; 137:525–529; Marti H. P., et al., "Homology cloning of rat 72 kDa type IV collagenase: Cytokine and second-messenger inducibility in mesangial cells," *Biochem. J.,* 1993;291:441– 446; Marti H. P., et al., "Transforming growth factor-b stimulates glomerular mesangial cell synthesis of the 72 kDa type IV collagenase," *Am. J. Pathol.,* 1994;144:82–94). These metalloprotroteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," Lab. Invest., 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," *Am. J. Pathol.*, 1992;141:85–98).

Unfortunately at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the renin-angiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.,* 1990;50:6184–6191; Marti H. P., et al., "Homology cloning of rat 72 kDa type IV collagenase: Cytokine and second-messenger inducibility in mesangial cells," *Biochem. J.,* 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M., et al., "Gene transfer of metalloproteinase transin induces aberrant behaviour of cultured mesangial cells," *Kidney Int.,* 1994;45:1580–1586; Turck J., et al., "Matrix metalloproteinase 2 (gelatinase A) regulates glomerular mesangial cell proliferation and differentiation," *J. Biol. Chem.,* 1996;271:15074–15083).

Inhibitors of MMP (MMPi) clearly have potential clinical applications in a host of diseases characterized by disturbance of extracellular matrix-cell interactions resulting in abnormal tissue remodeling (Vincenti M. P., et al., "Using inhibitors of metalloproteinases to treat arthritis," Arthritis Rheum., 1994;8: 1115–1126; Grams F., et al., "X-ray structures of human neutrophil collagenase complexed with peptide hydroxyamate and peptide thiol inhibitors. Implications for substrate binding and rational drug design," *Eur. J. Biochem.,* 1995;228:830–841).

We have identified a series of fluorine-substituted biphenyl butyric acid compounds and derivatives that are inhibitors of matrix metalloproteinases, particularly stromelysin-1, gelatinase A, and collagenase-3, and thus useful as agents for the treatment of atherosclerotic plaque rupture, aortic aneurism, heart failure, restenosis, periodontal disease, corneal ulceration, treatment of burns, decubital ulcers, wound repair, cancer, inflammation, pain, arthritis, osteoporosis, multiple sclerosis, renal disease, and other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

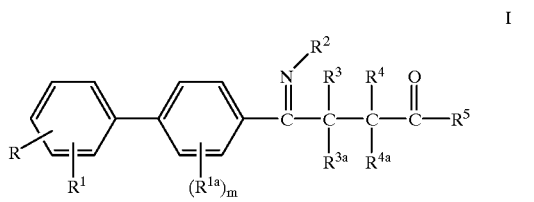

wherein R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
alkyl,
aryl,
arylalkyl,
heteroaryl, or
cycloalkyl,

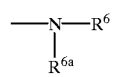

wherein $R^6$ and $R^{6a}$ are the same or different and are as defined above for $R^6$,

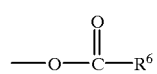

wherein $R^6$ is as defined above,

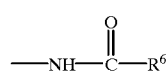

wherein $R^6$ is as defined above,

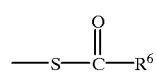

wherein $R^6$ is as defined above,

—SR⁶ wherein R⁶ is as defined above,

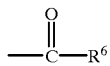

wherein R⁶ is as defined above,
—CH₂—OR⁶ wherein R⁶ is as defined above,

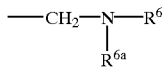

wherein R⁶ and R⁶ᵃ are the same or different and are as defined above for R⁶,

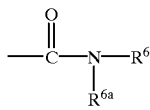

wherein R⁶ and R⁶ᵃ are the same or different and are as defined above for R⁶,

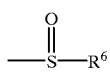

wherein R⁶ is as defined above,

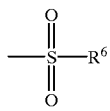

wherein R⁶ is as defined above,
cycloalkyl, or
heteroaryl;
R¹ᵃ is fluorine;
m is an integer of from 1 to 4;
R² is OR⁶ wherein R⁶ is as defined above, or

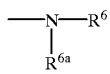

wherein R⁶ and R⁶ᵃ are the same or different and as defined above for R⁶;
R³, R³ᵃ, R⁴, and R⁴ᵃ are the same or different and are
hydrogen,
fluorine,
alkyl,
—(CH₂)ₙ-aryl wherein n is an integer from 1 to 6,
—(CH₂)ₙ-heteroaryl wherein n is as defined above,
—(CH₂)ₙ-cycloalkyl wherein n is as defined above,
—(CH₂)ₚ—X—(CH₂)q-aryl wherein X is O, S, SO, SO₂, or NH, and p and q are each zero or an integer of 1 to 6, and the sum of p+q is not greater than six,
—(CH₂)ₚ—X—(CH₂)q-heteroaryl wherein X, p, and q are as defined above,
or
—(CH₂)ₙ—R⁷ wherein R⁷ is
N-phthalimido,
N-2,3-naphthylimido, —OR⁶ wherein R⁶ is as defined above,

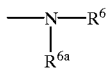

—SR⁶ wherein R⁶ and R⁶ᵃ are the same or different and are as defined above for R⁶,
—SR⁶ wherein R⁶ is as defined above,

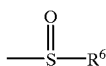

wherein R⁶ is as defined above,

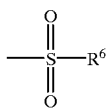

wherein R⁶ is as defined above,

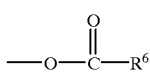

wherein R⁶ is as defined above,

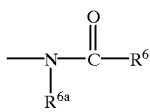

wherein R⁶ and R⁶ᵃ are the same or different and are as defined above for R⁶,

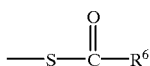

wherein R⁶ is as defined above,

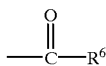

wherein R⁶ is as defined above,

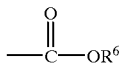

wherein R⁶ is as defined above, or

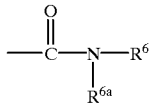

wherein R⁶ and R⁶ᵃ are the same or different and are as defined above for R⁶, and n is as defined above;

$R^5$ is OH, SH, or $OR^{5a}$ wherein $R^{5a}$ is alkyl, arylalkyl, cycloalkyl, or acyloxymethyl; with the proviso that $R^3$, $R^{3a}$, $R^4$, and $R^{4a}$ are hydrogen or at least one of $R^3$, $R^{3a}$, $R^4$, or $R^{4a}$ is fluorine;

and corresponding isomers thereof; or a pharmaceutically acceptable salt thereof.

A second aspect of the present invention is a compound of Formula II

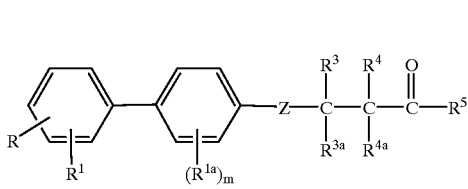

wherein R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
alkyl,
aryl,
arylalkyl,
heteroaryl, or
cycloalkyl,

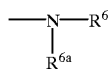

wherein $R^6$ and $R^{6a}$ are the same or different and are as defined above for $R^6$,

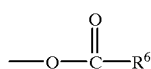

wherein $R^6$ is as defined above,

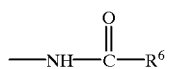

wherein $R^6$ is as defined above,

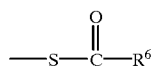

wherein $R^6$ is as defined above,
—$SR^6$ wherein $R^6$ is as defined above,

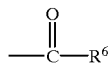

wherein $R^6$ is as defined above,

—$CH_2$—$OR^6$ wherein $R^6$ is as defined above,

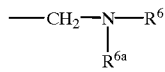

wherein $R^6$ and $R^{6a}$ are the same or different and are as defined above for $R^6$,

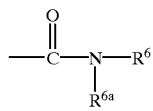

wherein $R^6$ and $R^{6a}$ are the same or different and are as defined above for $R^6$,

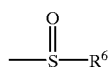

wherein $R^6$ is as defined above,

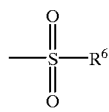

wherein $R^6$ is as defined above,
cycloalkyl, or
heteroaryl;
$R^{1a}$ is fluorine;
m is an integer of from 1 to 4;

Z is 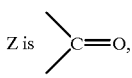

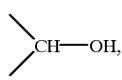

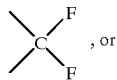, or

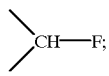

$R^3$, $R^{3a}$, $R^4$, and $R^{4a}$ are the same or different and are
hydrogen,
fluorine,
alkyl, —$(CH_2)_n$-aryl wherein n is an integer from 1 to 6,
—$(CH_2)_n$-heteroaryl wherein n is as defined above,
—$(CH_2)_n$-cycloalkyl wherein n is as defined above,
—$(CH_2)_p$—X—$(CH_2)_q$-aryl wherein X is O, S, SO, $SO_2$, or NH, and p and q are each zero or an integer of 1 to 6, and the sum of p+q is not greater than six,
—$(CH_2)_p$—X—$(CH_2)_q$-heteroaryl wherein X, p, and q are as defined above.

or

—$(CH_2)_n$—$R^7$ wherein $R^7$ is
N-phthalimido,
N-2,3-naphthylimido,
—$OR^6$ wherein $R^6$ is as defined above,

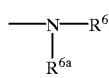

wherein $R^6$ and $R^{6a}$ are the same or different and are as defined above for $R^6$,
—$SR^6$ wherein $R^6$ is as defined above,

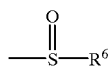

wherein $R^6$ is as defined above,

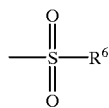

wherein $R^6$ is as defined above,

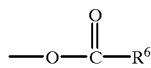

wherein $R^6$ is as defined above,

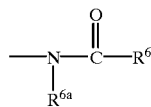

wherein $R^6$ and $R^{6a}$ are the same or different and are as defined above for $R^6$,

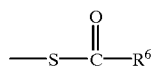

wherein $R^6$ is as defined above,

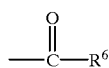

wherein $R^6$ is as defined above,

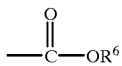

wherein $R^6$ is as defined above, or

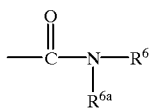

wherein $R^6$ and $R^{6a}$ are the same or different and are as defined above for $R^6$, and n is as defined above;

$R^5$ is OH, SH, or $OR^{5a}$ wherein $R^{5a}$ is alkyl, arylalkyl, cycloalkyl, or acyloxymethyl;

with the proviso that at least one of $R^3$, $R^{3a}$, $R^4$, or $R^{4a}$ is fluorine;

and corresponding isomers thereof; or a pharmaceutically acceptable salt thereof.

As matrix metalloproteinase inhibitors, the compounds of Formula I and Formula II are useful as agents for the treatment of multiple sclerosis. They are also useful as agents for the treatment of atherosclerotic plaque rupture, aortic aneurism, heart failure, restenosis, periodontal disease, corneal ulceration, treatment of burns, decubital ulcers, wound repair, cancer, inflammation, pain, arthritis, osteoporosis, renal disease, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I or Formula II in unit dosage form in the treatment methods mentioned above. Finally, the present invention is directed to methods for production of compounds of Formula I.

DETAILED DESCRIPTION OF THE INVENTION

In the compounds of Formula I and Formula II, the term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy,

as defined above for alkyl,

as defined above for alkyl,

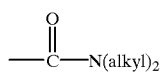

as defined above for alkyl, —(CH$_2$)$_{n^2}$—NH$_2$ wherein n$^2$ is an integer of 1 to 5, —(CH$_2$)$_{n^2}$—NH-alkyl as defined above for alkyl and n$^2$, —(CH$_2$)$_{n^2}$—N(alkyl)$_2$ as defined above for alkyl and n$^2$,

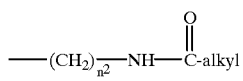

as defined above for alkyl and n$^2$ and

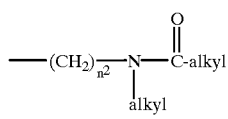

as defined above for alkyl and n$^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "acyloxymethyl" means a group of the formula

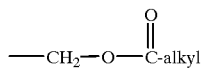

wherein alkyl is as defined above.

The term "heteroaryl" means a heteroaromatic radical and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl.

"Halogen" is fluorine, chlorine, bromine, or iodine.

"Alkali metal" is a metal in Group IA of the periodic table and includes, for example, lithium, sodium, potassium, and the like.

Some of the compounds of Formula I and Formula II wherein R$^5$ is OH are capable of further forming pharmaceutically acceptable carboxylic esters which are suitable as prodrugs. All of these carboxylic esters are within the scope of the present invention.

Pharmaceutically acceptable carboxylic esters of compounds of Formula I and Formula II include alkyl, cycloalkyl, arylalkyl, or acyloxymethyl esters.

The alkyl, cycloalkyl, and arylalkyl carboxylic esters of compounds of Formula I and Formula II can be prepared by methods known to one skilled in the art. For example, the corresponding carboxylic acids can be allowed to react directly with a suitable alcohol in the presence of a suitable acid catalyst to give the carboxylic esters. Alternatively, the carboxylic acids can be allowed to react with one of a number of suitable activating agents, which are known to one skilled in the art, followed by reaction with a suitable alcohol to give the carboxylic esters. Additionally for the 4-hydroxyimino-butyric acids of the present invention, the carboxylic acids can be allowed to cyclo-dehydrate using one of a number of methods known to one skilled in the art to give a cyclic 4,5-dihydro-6-oxo-6H-1,2-oxazine intermediate, which can be allowed to react with a suitable alcohol optionally in the presence of a suitable acid or base catalyst to give the carboxylic esters.

The acyloxymethyl esters of compounds of Formula I and Formula II can be prepared by methods known to one skilled in the art. For example, the corresponding carboxylic acids can be allowed to react first with a suitable base to give the carboxylate anion, followed by reaction with a carboxylic halomethyl ester, which can be obtained from commercial suppliers or prepared by methods known to one skilled in the art, optionally in the presence of a suitable agent to activate the carboxylic halomethyl ester, which are known to one skilled in the art, to give the acyloxymethyl esters.

Some of the compounds of Formula I and Formula II are capable of further forming both pharmaceutically acceptable acid addition and/or base salts. All of these forms are within the scope of the present invention.

Pharmaceutically acceptable acid addition salts of the compounds of Formula I and Formula II include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts", *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts", *J. of Pharma Sci.,* 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

In the first embodiment of the invention, a preferred compound of Formula I is one wherein $R^2$ is $OR^6$.

In the first embodiment of the invention, a more preferred compound of Formula I is one wherein $R^2$ is $OCH_3$.

In the first embodiment of the invention, a most preferred compound of Formula I is one wherein $R^2$ is OH, and $R^3$, $R^{3a}$, $R^4$, and $R^{4a}$ are hydrogen.

In the first embodiment of the invention, another more preferred compound of Formula I is one wherein $R^2$ is OH, and at least one of $R^3$, $R^{3a}$, $R^4$, and $R^{4a}$ is fluorine.

Particularly valuable in the first embodiment of the invention is a compound selected from the group consisting of:
4-(2-Fluoro-biphenyl-4-yl)-4-hydroxyimino-butyric acid;
4-(3-Fluoro-biphenyl-4-yl)-4-hydroxyimino-butyric acid;
4-(4'-Chloro-2-fluoro-biphenyl-4-yl)-4-methoxyimino-butyric acid;
4-(4'-Chloro-3-fluoro-biphenyl-4-yl)-methoxyimino-butyric acid;
4-(4'-Chloro-2-fluoro-biphenyl-4-yl)-4-hydroxyimino-butyric acid;
4-(4'-Chloro-3-fluoro-biphenyl-4-yl)-hydroxyimino-butyric acid;
4-(4'-Chloro-2,3-difluoro-biphenyl-4-yl)-4-hydroxyimino-butyric acid;
4-(4'-Chloro-2,6-difluoro-biphenyl-4-yl)-4-hydroxyimino-butyric acid;
4-(4'-Chloro-3,5-difluoro-biphenyl-4-yl)-4-hydroxyimino-butyric acid;
4-(4'-Chloro-2,3,5-trifluoro-biphenyl-4-yl)-4-hydroxyimino-butyric acid;
4-(4'-Chloro-2,3,6-trifluoro-biphenyl-4-yl)-4hydroxyimino-butyric acid;
4-(4'-Chloro-2,3,5,6-tetrafluoro-biphenyl-4-yl)-4-hydroxyimino-butyric acid;
4-(4'-Bromo-2-fluoro-biphenyl-4-yl)-4-hydroxyimino-butyric acid;
4-(4'-Bromo-3-trifluoro-biphenyl-4-yl)-4-hydroxyimino-butyric acid;
4-(4'-Chloro-2-fluoro-biphenyl-4-yl)-4-hydroxyimino-butyric acid;
4-(4'-Chloro-3-fluoro-biphenyl-4-yl)-4-hydroxyimino-butyric acid;
4-(2,4'-Difluoro-biphenyl-4-yl)-4-hydroxyimino-butyric acid;
4-(3,4'-Difluoro-biphenyl-4-yl)-4-hydroxyimino-butyric acid;
4-(2,3'-Difluoro-biphenyl-4-yl)-4-hydroxyimino-butyric acid;
4-(3,3'-Difluoro-biphenyl-4-yl)-4-hydroxyimino-butyric acid;
4-(2,2'-Difluoro-biphenyl-4-yl)-4-hydroxyimino-butyric acid;
4-(2',3-Difluoro-biphenyl-4-yl)-4-hydroxyimino-butyric acid;
4-(4'-Cyano-2-fluoro-biphenyl-4-yl)-4-hydroxyimino-butyric acid;
4-(4'-Cyano-3-fluoro-biphenyl-4-yl)-4-hydroxyimino-butyric acid;
4-(2-Fluoro-4'-methoxy-biphenyl-4-yl)-4-hydroxyimino-butyric acid;
4-(3-Fluoro-4'-methoxy-biphenyl-4-yl)-4-hydroxyimino-butyric acid;
4-(2-Fluoro-4'-methyl-biphenyl-4-yl)-4-hydroxyimino-butyric acid;
4-(3-Fluoro-4'-methyl-biphenyl-4-yl)-4-hydroxyimino-butyric acid;
4-(2-Fluoro-4'-hydroxy-biphenyl-4-yl)-4-hydroxyimino-butyric acid;
4-(3-Fluoro-4'-hydroxy-biphenyl-4-yl)-4-hydroxyimino-butyric acid;
4-(2-Fluoro-4'-methylsulfanyl-biphenyl-4-yl)-4-hydroxyimino-butyric acid;
4-(3-Fluoro-4'-methylsulfanyl-biphenyl-4-yl)-4-hydroxyimino-butyric acid;
4-(2-Fluoro-4'-trifluoromethyl-biphenyl-4-yl)-4-hydroxyimino-butyric acid;
4-(3-Fluoro-4'-trifluoromethyl-biphenyl-4-yl)-4-hydroxyimino-butyric acid;
(±)-4-(4'-Chloro-2-fluoro-biphenyl-4-yl)-2-fluoro-2-(3-phenylpropyl)-4-hydroxyimino-butyric acid;
(±)-4-(4'-Chloro-3-fluoro-biphenyl-4-yl)-2-fluoro-2-(3-phenylpropyl)-4-hydroxyimino-butyric acid;
(±)-4-(4'-Chloro-2-fluoro-biphenyl-4-yl)-2-fluoro-2-(2-phenylethyl)-4-hydroxyimino-butyric acid;
(±)-4-(4'-Chloro-3-fluoro-biphenyl-4-yl)-2-fluoro-2-(2-phenylethyl)-4-hydroxyimino-butyric acid;
(±)-4-(4'-Chloro-2-fluoro-biphenyl-4-yl)-2-fluoro-2-(3-phthalimidopropyl)-4-hydroxyimino-butyric acid;
(±)-4-(4'-Chloro-3-fluoro-biphenyl-4-yl)-2-fluoro-2-(3-phthalimidopropyl)-4-hydroxyimino-butyric acid;
(±)-4-(4'-Chloro-2-fluoro-biphenyl-4-yl)-2-fluoro-2-(1H-indol-3-yl)methyl-4-hydroxyimino-butyric acid;
(±)-4-(4'-Chloro-3-fluoro-biphenyl-4-yl)-2-fluoro-2-(1H-indol-3-yl)methyl-4-hydroxyimino-butyric acid;
(±)-4-(4'-Chloro-2-fluoro-biphenyl-4-yl)-2-(2,4-dioxo-1,5,5-trimethyl-imidazolidin-3-yl)methyl-2-fluoro-4-hydroxyimino-butyric acid; and
(±)-4-(4'-Chloro-3-fluoro-biphenyl-4-yl)-2-(2,4-dioxo-1,5,5-trimethyl-imidazolidin-3-yl)methyl-2-fluoro-4-hydroxyimino-butyric acid;
and corresponding isomers thereof; or a pharmaceutically acceptable salt thereof.

Most particularly valuable in the first embodiment of the invention are 4-(2-Fluoro-biphenyl-4-yl)-4-hydroxyiminobutyric acid; 4-(3-Fluoro-biphenyl-4-yl)-4-hydroxyimino-butyric acid; 4-(4'-Chloro-2-fluoro-biphenyl-4-yl)-4-hydroxyimino-butyric acid; and 4-(4'-Chloro-3-fluoro-biphenyl-4-yl)-4-hydroxyimino-butyric acid.

In the second embodiment of the invention, a preferred compound of Formula II is one wherein

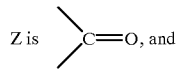

$R^3$ and $R^{3a}$ are fluorine.

In another second embodiment of the invention, a preferred compound of Formula II is one wherein

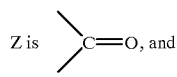

$R^4$ and $R^{4a}$ are fluorine.

In a second embodiment of the invention, a more preferred compound of Formula II is one wherein

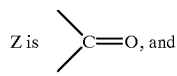

$R^3$ is fluorine.

In a second embodiment of the invention, another more preferred compound of Formula II is one wherein

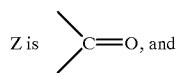

$R^4$ is fluorine.

In another second embodiment of the invention, a preferred compound of Formula II is one wherein

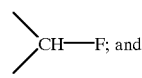

$R^3$ and $R^{3a}$ are fluorine.

In another second embodiment of the invention, a preferred compound of Formula II is one wherein

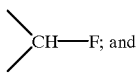

$R^4$ and $R^{4a}$ are fluorine.

In another second embodiment of the invention, a preferred compound of Formula II is one wherein

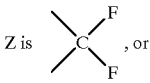

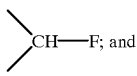

$R^3$ is fluorine.

In another second embodiment of the invention, a preferred compound of Formula II is one wherein

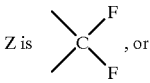

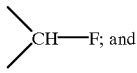

$R^4$ is fluorine.

Particularly valuable in the second embodiment of the invention is a compound selected from the group consisting of:

4-(2-Fluoro-biphenyl-4-yl)-4-oxo-butyric acid;
4-(3-Fluoro-biphenyl-4-yl)-4-oxo-butyric acid;
(±)-4-(4'-Chloro-2-fluoro-biphenyl-4-yl)-4-hydroxy-butyric acid;
(±)-4-(4'-Chloro-3-fluoro-biphenyl-4-yl)-4-hydroxy-butyric acid;
(±)-4-(4'-Chloro-2-fluoro-biphenyl-4-yl)-3-fluoro-4-oxo-butyric acid; and
(±)-4-(4'-Chloro-3-fluoro-biphenyl-4-yl)-3-fluoro-4-oxo-butyric acid;
and corresponding isomers thereof; or a pharmaceutically acceptable salt thereof.

The compounds of Formula I and Formula II are valuable inhibitors of gelatinase A and/or stromelysin-1 and/or collagenase-3. It has been shown previously that inhibitors of matrix metalloproteinases have efficacy in models of disease states like arthritis and metastasis that depend on modification of the extracellular matrix.

In vitro experiments can be carried out to demonstrate the efficacy of compounds of Formula I and Formula II as potent and specific inhibitors of gelatinase A and stromelysin-1. Experiments can be carried out with the catalytic domains of the proteinases. $IC_{50}$ values can be determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*", *Biochemistry*, 1992;31:11231–11235).

Experimental Autoimmune Encephalomyelitis (EAE)

Compounds can be administered by oral route to mice sensitized with a fragment of mouse myelin basic protein to induce EAE. Mice can be dosed daily for 21 days beginning 4 hours before sensitization on day one. EAE responses of compound treated groups can be compared to those of a control group of mice sensitized identically and a sham-sensitized group treated with vehicle.

Methods

Sensitization Female mice [PL/J(F1)×SJL/J, Jackson Labs], 11 weeks old, can be sensitized s.c. (0.05 cc×2) at the base of the tail with an emulsion containing equal parts of mouse myelin basic protein (MBP) fragment (amino acids 1–9 of the N-terminus of MBP) in saline and Difco Complete Freund's Adjuvant (CFA) fortified with heat killed desiccated *Mycobacteria tuberculosis* (MT). Each mouse will receive 300 μg of MBP fragment (230 μg free base) and 200 μg MT followed by retrobulbar (IV) injection of 200 ng of *B. pertussis* toxin in 0.2 cc of saline. Two days later mice receive a second injection of *B. pertussis* toxin.

Neurological Assessment

Animals can be weighed and evaluated for symptoms of EAE before and frequently after sensitization. EAE score: (0.5=slight limp tail, 1=limp tail or slow to right, 1.5=slight limp tail and slow to right, 2=paresis/mild paralysis or incontinence, 2.5=mild paralysis and slow to right or complete paralysis (one hind limb), 3=hind limb paralysis (both), 3.5=hind limb paralysis (both) and limp torso; 4=additional fore limb paralysis, 4.5=head movement only, 5=moribund, death after previous EAE symptoms). Evaluators are blinded as to compound treatments and previous behavioral scores.

Disease symptoms can be compared among groups for EAE severity, incidence, time to onset, cumulative score, and deaths. Peak EAE score: the mean of the highest score for each mouse in a group, independent of duration of symptoms; EAE incidence: the mean number of mice showing symptoms of EAE, defined as having EAE scores on any 3 consecutive days that total "≧3.0". EAE deaths: an animal that died must have presented previous evidence of an EAE score greater than 0.5; EAE onset: the first of a 3-day series scoring a total of ≧3.0.

A Cumulative EAE score is calculated for each animal. A mean of all animals' cumulative scores is then determined for each day.

Experimental groups are assumed to be similar and are compared for statistical significance by a 2-tailed T-Test (p≦0.05).

Compound can be homogenized manually with an aliquot of warm vehicle (1.0% hydroxypropyl-methylcellulose [Sigma] in water) in glass mortar tubes and homogenizing pestle. The smooth compound is gradually suspended in vehicle. Mice can be dosed with compound and/or vehicle, 10 mL/kg in groups often. A sham-sensitized group can be similarly dosed with vehicle.

Streptococcal Cell Wall Model (SCW)

Female Lewis rats (125–150 g) can be sensitized to the 100P preparation of streptococcal cell walls (obtained from Lee Labs, Greyson, Ga.) with an intra-articular injection of 10 μL SCW containing 6 μg of the cell wall particles into one of the ankle joints. The contralateral ankle joint can be injected with an equal volume of saline. Twenty-one days later, animals are placed in treatment groups (7 per group) according to their immediate response to the intra-articular injection of SCW (to obtain groups with equivalent responses). A control group is injected with saline. Each animal is then lightly anesthetized with ether, the paw volumes of each hind paw are determined by mercury plethysmography, and the animals are injected IV via the tail vein with a 0.25-mL dose of SCW containing 100 μg of the 100P cell wall particles. Each group of rats receives an oral dose of compound for 7 days in an appropriate dosing vehicle beginning on Day 21.

Paw swelling is determined by subtracting the paw volume of the saline injected ankle from the SCW sensitized ankle. Percent inhibition is calculated by comparing the compound treatment group with the control group. A one-way analysis of variance with a Dunnett's test for multiple comparisons is used for determination of statistical power.

Rats can be sensitized 21 days prior to initiating the flare response by systemic SCW. Compound can be given 1 hour before to SCW and again 2 hours later for 4 consecutive days. Paw volume is measured 24 hours after the first administration. Numbers represent the mean percent inhibition of swelling from 10 animals/treatment group.

Adjuvant Arthritis Model

Polyarthritis can be induced by a modified method of the procedure developed by Chang, et al., *Arthritis and Rheum.*, 1980;23:62. Briefly, male Wistar rats (100–115 g each) receive subcutaneous injection of 0.1 mL of 10 mg/mL (or 1 mg) *Mycobacterium butyricum* suspended in paraffin oil in the distal third of the tail, using a glass tuberculin syringe and 25 gauge needle. *M. butyricum* suspension is achieved by sonication in paraffin oil for 10 minutes with the vessel immersed in ice bath. Rats are randomized after injection and placed in cages. On Day 12 following immunization, rats with the highest paw swelling as well as those that showed no swelling at all are culled. The rest are randomized and separated into dosing (test) groups (N=10 per group) and control (vehicle) group (N=20). The hind paws volume and the weights of each animal in each group is recorded and served as the initial values for the study. Hind paw swelling is assessed using mercury plethysmography beginning on Day 12 and every other day till Day 22 (final assessment).

Compound can be tested at 6, 20, and 60 mg/kg divided into two equal doses per day and suspended in 1% methyl cellulose (2% viscosity, 1500 centipoises, Sigma). The dose volume is 10 mL/kg PO. Animals are dosed twice daily for 10 days starting on Day 12. Also, hind paw volumes are measured on Days 12, 14, 16, 18, 20, and 22 as stated above. The results are reported as % inhibition of delta edema on Day 22. Delta edema is the difference in footpad edema between the day in which animals are assessed and that on Day 12 of the study. The percent inhibition is based on a comparison of the treatment groups to the vehicle group.

Acetic Acid-Induced Hyperalgesia Model

Male Swiss-Webster mice (20–30 g) can be pretreated orally with vehicle or compound (0.03–10 mg/kg) 1 hour before the administration of 0.6% acetic acid (10 mL/kg i.p., in saline). Treatment groups (n=8) are divided so that 2 animals are placed into each of four 4"×4"×4" adjacent plexiglass containers. Seven minutes after acid, writhing motions (abdominal contractions, concave arching of the back, and/or hindleg stretching) are tallied for 5 minutes. The $ID_{40}$ value is calculated by linear regression analysis.

The following list contains abbreviations and acronyms used within the schemes and text:

Ni(dppf)Cl$_2$ 1,1'-Bis(diphenylphosphino)ferrocene nickel dichloride

Tf$_2$O Trifluoromethanesulfonic anhydride

Bu normal butyl n-Bu normal butyl

Tf Trifluoromethanesulfonyl

CNS Central nervous system

CH$_2$Cl$_2$ Dichloromethane
EAE Experimental autoimmune encephalomyelitis
MMP Matrix metalloproteinase
VSMC Vascular smooth muscle cell
TFA Trifluoroacetic acid
ClSnBu$_3$ Tributyltin chloride
IC$_{50}$ Concentration of compound required to inhibit 50% of enzyme activity
HCl Hydrogen chloride
KHMDS Potassium hexamethyldisilazide
n-BuLi n-butyl lithium
(Bu$_3$Sn)$_2$ Hexabutylditin
MnCl$_2$ Manganese chloride
THF Tetrahydrofuran
Pd(PPh)$_2$Cl$_2$ Bis(triphenylphosphine)palladium(II) chloride
H$_2$S Hydrogen sulfide
NaH Sodium hydride
LiOH Lithium hydroxide
H$_2$O$_2$ Hydrogen peroxide
H$_2$O Water
CDI 1,1'-Carbonyldiimidazole
NBS N-Bromosuccinimide
CCl$_4$ Carbon tetrachloride
hv Light
HBr Hydrogen bromide
KBr Potassium bromide
NaNO$_2$ Sodium nitrite
Me Methyl
Et Ethyl
t-Bu tertiary-butyl
Bn Benzyl
(COCl)$_2$ Oxalyl chloride
NFSI N-Fluorodibenzenesulfonamide
Et$_3$SiH Triethylsilane
LDA Lithium diisopropylamide
EtOH Ethanol
NaBH$_4$ Sodium borohydride
DAST Diethylamino sulfur trifluoride
TMS-Cl Chlorotrimethylsilane
DMF Dimethylformamide
KOH Potassium hydroxide
p-TsOH para-Toluenesulfonic acid
NaOH Sodium hydroxide
halo Chlorine, bromine, iodine, or fluorine
CHCl$_3$ Chloroform
E Entgegen
Z Zusammen
TIMPs Tissue inhibitors of matrix metalloproteinases
H$_2$NOH Hydroxylamine
NaHCO$_3$ Sodium bicarbonate
Na$_2$CO$_3$ Sodium carbonate
K$_2$CO$_3$ Potassium carbonate
TEA Triethylamine
B(OiPr)$_3$ Triisopropylborate
BF$_3$·OEt$_2$ Boron trifluoride etherate
Pd(PPh$_3$)$_4$ Tetrakis(triphenylphosphine)palladium(0)
Ph Phenyl
CDCl$_3$ Deuterated chloroform
DMSO-d$_6$ Deuterated dimethylsulfoxide
MgSO$_4$ Magnesium sulfate
Na$_2$SO$_4$ Sodium sulfate
CuCN Copper(I)cyanide
ZnCl$_2$ Zinc chloride
VCl$_3$ Vanadium chloride
FeCl$_3$ Ferric chloride Compounds of Formula I and Formula II wherein R$^{3a}$ and R$^{4a}$ are hydrogen, Z is 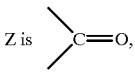

R$^5$ is OH or SH, and R, R$^1$, R$^2$, R$^3$, and R$^4$ are as defined above can be made by one of three general routes, as set forth in Scheme 1.

Route A involves reaction of a compound of Formula (1), commercially obtained or prepared according to methods known to one skilled in the art with a compound of Formula (2), commercially obtained or prepared according to methods known to one skilled in the art in the presence of a suitable catalyst such as, for example, tetrakis (triphenylphosphine)-palladium(0), bis(triphenylphosphine) palladium(II)chloride, and the like with or without sodium bicarbonate to give a compound of Formula (3). A compound of Formula (3) can be reacted with a suitable metallating agent such as, for example, n-butyl lithium and the like to generate an organolithium in situ, which in turn can be reacted with a suitable metallating agent such as, for example, MnCl$_2$, CuCN, ZnCl$_2$, VCl$_3$, and the like to generate a modified organometallic agent in situ, followed by reaction with a compound of Formula (4) to give a compound of Formula (5). Alternatively, a compound of Formula (3) can be reacted with a suitable metallating agent such as, for example, n-butyl lithium, magnesium metal, and the like to generate an organolithium or organomagnesium salt in situ, followed by reaction of the salt with a suitable metallating reagent such as, for example, tri-(n-butyl)tin chloride, triisopropylborate, and the like to give a compound of Formula (6). Alternatively, a compound of Formula (6) may be prepared by reacting a compound of Formula (3) with hexabutylditin in the presence of a suitable catalyst such as, for example, tetrakis(triphenylphosphine)-palladium(0) in a suitable solvent such as, for example, benzene or toluene at temperatures between about 25° C. and reflux. A compound of Formula (6) can be coupled with a compound of Formula (4) in the presence of a suitable catalyst such as, for example, tetrakis(triphenylphosphine) palladium(0), bis(triphenylphosphine)palladium(II)chloride and the like with or without sodium bicarbonate to give a compound of Formula (5).

A compound of Formula (5) can be deprotected using standard methodology known to one skilled in the art to give the corresponding carboxylic acid, which then can be condensed with a compound of Formula (7) to give a compound of Formula Ia. Alternatively, a compound of Formula (5) can be deprotected using standard methodology known to one skilled in the art, and the resulting carboxylic acid coupled with hydrogen sulfide after pretreatment with a suitable coupling agent such as, for example, 1,1'-carbonyldiimidazole (CDI), isobutyryl chloride, and the like, and then condensed with a compound of Formula (7) to give a compound of Formula Ib.

Route B involves reaction of a compound of Formula (8) with a suitable metallating agent such as, for example, n-butyl lithium, magnesium metal, and the like to generate an organolithium or organomagnesium salt in situ, followed by reaction of the salt with a suitable tin metallating reagent such as, for example, tri-(n-butyl)tin chloride and the like to give a compound of Formula (9). A compound of Formula (9) can be coupled with a compound of Formula (4) in the presence of a suitable catalyst such as, for example, tetrakis (triphenylphosphine)-palladium(0), bis(triphenylphosphine) palladium(II)chloride, and the like with or without sodium bicarbonate to give a compound of Formula (10). A compound of Formula (10), wherein $R^9$ is $PG_2O$, can be deprotected using standard methodology known to one skilled in the art to give the corresponding free phenol, which can be reacted with trifluoromethanesulfonic anhydride to give the corresponding trifluoromethylsulfonyloxy derivative, which can be coupled with a compound of Formula (1) in the presence of a suitable catalyst such as, for example, tetrakis (triphenylphosphine)palladium(0), bis(triphenylphosphine)-palladium(II)chloride, and the like with or without sodium bicarbonate to give a compound of Formula (5). Alternatively, a compound of Formula (10), wherein $R^9$ is chlorine, can be reacted with a compound of Formula (11), obtained commercially or prepared according to methods known to one skilled in the art, in the presence of a suitable catalyst such as, for example, 1,1'-bis(diphenylphosphino) ferrocene nickel dichloride and the like to give a compound of Formula (5). A compound of Formula (5) can be converted to compounds of Formulas Ia and Ib according to the methods outlined for Route A.

A compound of Formula (4) can be synthesized according to the sequence outlined in Scheme 2.

In Scheme 2, (R)- or (S)-4-benzyl-2-oxazolidinone can be reacted with an acid chloride (12), prepared using standard methodology known to one skilled in the art, in the presence of a non-nucleophilic base such as, for example, sodium hydride and the like in an inert solvent such as, for example, tetrahydrofuran and the like at temperatures between about −40° C. and about reflux to give the N-acyl-oxazolidinone (13). The N-acyl-oxazolidinone (13) can be reacted with a suitable base such as, for example, potassium hexamethyldisilazide (KHDMS), lithium diisopropylamide (LDA), and the like followed by a bromoester (14), prepared in racemic form by bromination of the corresponding ester (15) with a suitable brominating reagent such as, for example, N-bromosuccinamide (NBS) and the like in a suitable solvent such as, for example, carbon tetrachloride and the like in the presence of ultraviolet light and a peroxide such as, for example, benzoyl peroxide and the like or in chiral form by reaction of an amino acid (16) with sodium nitrite and potassium bromide in aqueous hydrobromic acid followed by reacting the resulting bromoacid with a suitable coupling agent such as, for example, CDI, DCC, i-$C_4H_9$OCOCl, and the like and reacting the activated acid with a suitable alcohol such as, for example, methanol, ethanol, benzyl alcohol, and the like to give a compound of Formula (17). A compound of Formula (17), which may exist as a mixture of diastereoisomers, can be purified by a suitable technique such as, for example, chromatography on silica gel, and the like to give pure stereoisomers, which can be reacted with lithium hydroperoxide in THF-water followed by reaction of the resulting carboxylic acid with oxalyl chloride to give the corresponding acid chloride (4).

Alternatively, compounds of Formula I and Formula II wherein Z is

$R^5$ is OH or SH, and R, $R^1$, $R^2$, $R^3$, $R^{3a}$, $R^4$, and $R^{4a}$ are as defined in Formula I and Formula II can be synthesized according to the sequence outlined in Scheme 3.

In Scheme 3 the biphenyl (3), prepared according to the procedures outlined in Scheme 1, is allowed to react with a suitable acylating agent such as, for example, the acid chloride of Formula (12) according to the method described in Scheme 1, Route A for the reaction of a compound of Formula (3) with a compound of Formula (4) to give a compound of Formula (18). A compound of Formula (18) is allowed to react with a suitable strong base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (19), or N-fluorodibenzenesulfonamide (NFSI) for $R^{3a}$ equals fluorine, at temperatures at about −78° C. to about 50° C. to give a compound of Formula (20). A compound of Formula (20) is allowed to react with a suitable strong base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (21) to give a compound of Formula (22). A compound of Formula (22) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (23). A compound of Formula (23) is condensed with a compound of Formula (7) to give a compound of Formula (Ic). Alternatively, a compound of Formula (23) is allowed to react with hydrogen sulfide after pretreatment with a suitable coupling agent such as, for example, 1,1'-carbonyldiimidazole (CDI), N,N'-dicyclohexylcarbodiimide isobutyryl chloride, and the like, and then condensed with a compound of Formula (7) to give a compound of Formula (Id).

Alternatively, a compound of Formula (22) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (24) or NFSI for $R^4$ equals fluorine, at temperatures at about −78° C. to about 50° C. to give a compound of Formula (25). A compound of Formula (25) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (26). A compound of Formula (26) is converted to compounds of Formulas (Ie) and (If) according to the procedure described for the conversion of a compound of Formula (23) to compounds of Formulas (Ic) and (Id), respectively.

Alternatively, a compound of Formula (25) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (27) or NFSI for $R^{4a}$ equals fluorine, at temperatures at about −78° C. to about 50° C. to give a compound of Formula (28). A compound of Formula (28) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid is resolved using methods known to one skilled in the art to give a compound of Formula (29). A compound of Formula (29) is converted to compounds of Formulas (Ig) and (Ih) according to the procedure described for the conversion of a compound of Formula (23) to compounds of Formulas (Ic) and (Id), respectively.

Alternatively, compounds of Formula I and Formula II wherein Z is

$R^5$ is OH or SH, and R, $R^1$, $R^2$, $R^3$, $R^{3a}$, $R^4$, and $R^{4a}$ are as defined in Formula I and Formula II are synthesized according to the sequence outlined in Scheme 4.

In Scheme 4, a compound of Formula (30) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (27) or NFSI for $R^{4a}$ equals fluorine, at temperatures at about −78° C. to about 50° C. to give a compound of Formula (31). A compound of Formula (31) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (32), prepared by allowing a compound of Formula (3), prepared according to the method outlined in Scheme 1, to react with a suitable acylating agent such as $BrCH_2COCl$ according to the method described in Scheme 1, Route A for the reaction of a compound of Formula (3) with a compound of Formula (4), to give a compound of Formula (33). A compound of Formula (33) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid can be resolved using methods known to one skilled in the art to give a compound of Formula (34). A compound of Formula (34) is converted to compounds of Formulas (Ii) and (Ij) according to the procedure described in Scheme 3 for the conversion of a compound of Formula (23) to compounds of Formulas (Ic) and (Id), respectively. Alternatively, a compound of Formula (33) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (35), or NFSI for $R^3$ equals fluorine, at temperatures at about −78° C. to about 50° C. to give a compound of Formula (36). A compound of Formula (36) is deprotected using appropriate conditions such as, for example, trifluoroacetic acid or anhydrous hydrogen chloride in a suitable solvent such as, for example, dichloromethane or chloroform, with or without a carbonium ion scavenger such as, for example, triethylsilane, and the resulting carboxylic acid can be resolved using methods known to one skilled in the art to give a compound of Formula (37). A compound of Formula (37) is converted to compounds of Formulas (Ik) and (Il) according to the procedure described in Scheme 3 for the conversion of a compound of Formula (23) to compounds of Formulas (Ic) and (Id), respectively. Alternatively, a compound of Formula (36) is allowed to react with a suitable base such as, for example, n-butyl lithium, lithium diisopropylamide, potassium hexamethyldisilazide, and the like in an inert solvent such as, for example, tetrahydrofuran, diethyl ether, and the like at about −78° C. to about 25° C. followed by a suitable alkylating agent of Formula (19), or NFSI for $R^{3a}$ equals fluorine, at temperatures at about −78° C. to about 50° C. to give a compound of Formula (28). A compound of Formula (28) is converted via a compound of Formula (29) to compounds of Formulas (Ig) and (Ih) according to the procedure described in Scheme 3.

Compounds of Formula II wherein Z is CH(OH), C=S, $CF_2$, or CHF and $R^5$ is OH or SH, and R, $R^1$, $R^3$, $R^{3a}$, $R^4$, and $R^{4a}$ are as defined in Formula II are synthesized according to the sequence outlined in Scheme 5.

In Scheme 5, keto-esters of Formulas (5), (22), (25), (28), (33), or (36) can be hydrolyzed to the corresponding keto-acids, such as by stirring in aqueous hydrochloric acid at a concentration between about 2M and about 6M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification, and the keto-acids can be reduced using an appropriate hydride donating reagent such as sodium borohydride in ethanol, L- or S-selectride and the like in a suitable solvent such as, for example, toluene, tetrahydrofuran and the like to give the alcohol-acid (38). The alcohol-acid (38) can be silylated such as, for example, by allowing it to react with chlorotrimethylsilane (TMS-Cl) in the presence of a catalyst such as, for example, imidazole and the like in a suitable solvent such as, for example, anhydrous dimethylformamide (DMF) and the like to give the corresponding O-silyl alcohol-silyl ester, which can be fluorinated by allowing it to react with a suitable reagent such as, for example, diethylaminosulfur trifluoride (DAST) and the like in a suitable solvent such as, for example, dichloromethane, chloroform and the like at temperatures between about −20° C. and about reflux to give the corresponding fluoro-silyl ester, which can be hydrolyzed by stirring in aqueous hydrochloric acid at a concentration between about 2M and about 6M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification or by stirring in the presence of a suitable fluoride reagent such as, for example, tetra-n-butylammonium fluoride, aqueous hydrogen fluoride and the like in a suitable solvent such as, for example, tetrahydrofuran, acetonitrile and the like to give the fluoro-acid (39). The fluoro-acid (39) can be reacted with a suitable coupling agent such as, for example, CDI, DCC, i-$C_4H_9OCOCl$, and the like followed by hydrogen sulfide to give the fluoro-thioacid (40).

Alternatively, the keto-esters of Formulas (5), (22), (25), (28), (33), or (36) can be allowed to react with a suitable fluorinating agent such as, for example, DAST and the like in a suitable solvent such as, for example, dichloromethane, chloroform and the like at temperatures between about −20° C. and about reflux to give the corresponding fluoro-ester, which can be hydrolyzed such as by stirring in aqueous hydrochloric acid at a concentration between about 2M and about 6M and at temperatures between about 25° C. and reflux or by stirring in the presence of a suitable alkali metal hydroxide such as, for example, lithium, sodium, potassium hydroxide and the like in a suitable solvent such as, for example, methanol, ethanol, aqueous THF and the like at temperatures between about 0° C. and reflux followed by acidification to give the corresponding difluoro-acid (41). The difluoro-acid (41) can be allowed to react with a suitable coupling agent such as, for example, CDI, DCC, i-$C_4H_9OCOCl$, and the like followed by hydrogen sulfide to give the fluoro-thioacid (42).

Alternatively, keto-esters of Formulas (5), (22), (25), (28), (33), or (36) can be hydrolyzed to the corresponding keto-acids, such as by stirring in aqueous hydrochloric acid at a concentration between about 2M and about 6M and at temperatures between about 25° C. and reflux or by stirring in the presence of a suitable alkali metal hydroxide such as, for example, lithium, sodium or potassium hydroxide and the like in a suitable solvent such as, for example, methanol, ethanol or aqueous THF and the like at temperatures between about 0° C. and reflux followed by acidification, and the keto-acids allowed to react with a suitable sulfur reagent such as, for example, Lawesson's reagent and the like in a suitable solvent such as, for example, tetrahydrofuran and the like at temperatures between about 0° C. and reflux to give the thioketo-acid (43). The thioketo-acid (43) can be allowed to react with a suitable coupling agent such as, for example, CDI, DCC, i-$C_4H_9OCOCl$, and the like followed by hydrogen sulfide to give the thioketo-thioacid (44).

Compounds of Formula I wherein $R^5$ is $R^{5a}$, $R^2$ is OH, and R, $R^1$, $R^3$, $R^{3a}$, $R^4$, and $R^{4a}$ are as defined in Formula I can be synthesized according to the sequence outlined in Scheme 6.

In Scheme 6, oxime-acids of Formulas (Ia), (Ic), (Ie), (Ig), (Ii), and (Ik), wherein $R^2$ is OH, can be cyclized by stirring in a suitable solvent such as, for example, toluene, benzene, and the like at about reflux over a Dean-Stark trap to remove water, or by stirring in a suitable solvent such as, for example, tetrahydrofuran, dioxane, toluene, dichloromethane and the like which contains a dehydrating agent such as, for example, anhydrous magnesium sulfate, activated 3 angstrom molecular sieves, and the like at temperatures from about 0° C. to about reflux, in the presence of a suitable acid catalyst such as, for example, p-toluenesulfonic acid or methanesulfonic acid and the like to give a compound of the Formula (45). Alternatively, the oxime-acids of Formulas (Ia), (Ic), (Ie), (Ig), (Ii), and (Ik) wherein $R^2$ is OH can be cyclized by reaction with a suitable carboxylic acid activating agent such as, for example, N,N'-dicyclohexyl-carbodiimide, 1,1'-carbonyldiimidazole, iso-butylchloroformate, 2-chloro-1-methyl-pyridinium iodide/triethylamine and the like in a suitable solvent such as, for example, tetrahydrofuran, dioxane, dichloromethane, and the like at about −20° C. to about reflux to give a compound of Formula (45). A compound of Formula (45) can be reacted with an alcohol of Formula $R^{5a}OH$ (46), wherein $R^{5a}$ is as defined in Formula I, in a suitable solvent such as, for example, chloroform, tetrahydrofuran, dioxane, toluene and the like optionally in the presence of a suitable acid catalyst such as hydrogen chloride, p-toluenesulfonic acid, sulfuric acid and the like at temperatures from about 25° C. to about reflux to give compounds of Formulas (47) and (48), wherein the conformations of the oximes are designated as E and Z, respectively.

Alternatively, oxime-acids of Formulas (Ia), (Ic), (Ie), (Ig), (Ii), and (Ik), wherein $R^2$ is as defined in Formula I, and compounds of Formula II wherein Z is as defined in Formula II, can be allowed to react with 1 mol equivalent of a suitable base such as, for example, potassium or sodium hydroxide and the like in a suitable solvent such as, for example, acetone, ethanol, water, and the like followed by reaction with an alkyl carboxylic acid, halomethyl ester of Formula (49) such as, for example, 2,2-dimethyl-propionic acid, bromomethyl ester or 2,2-dimethyl-propionic acid, chloromethyl ester, and the like optionally in the presence of a suitable activating agent such as, for example, 10% aqueous sodium iodide, aqueous silver nitrate and the like, in a suitable solvent such as, for example, acetone at temperatures between about 0° C. and about reflux to give compounds of Formulas (50) and (51), wherein the conformations of the oximes are designated as E and Z, respectively, and (52).

Compounds of the formula $H_2NR^2$ can be obtained from commercial sources or prepared by methods generally known to one skilled in the art.

SCHEME 1
Route A:
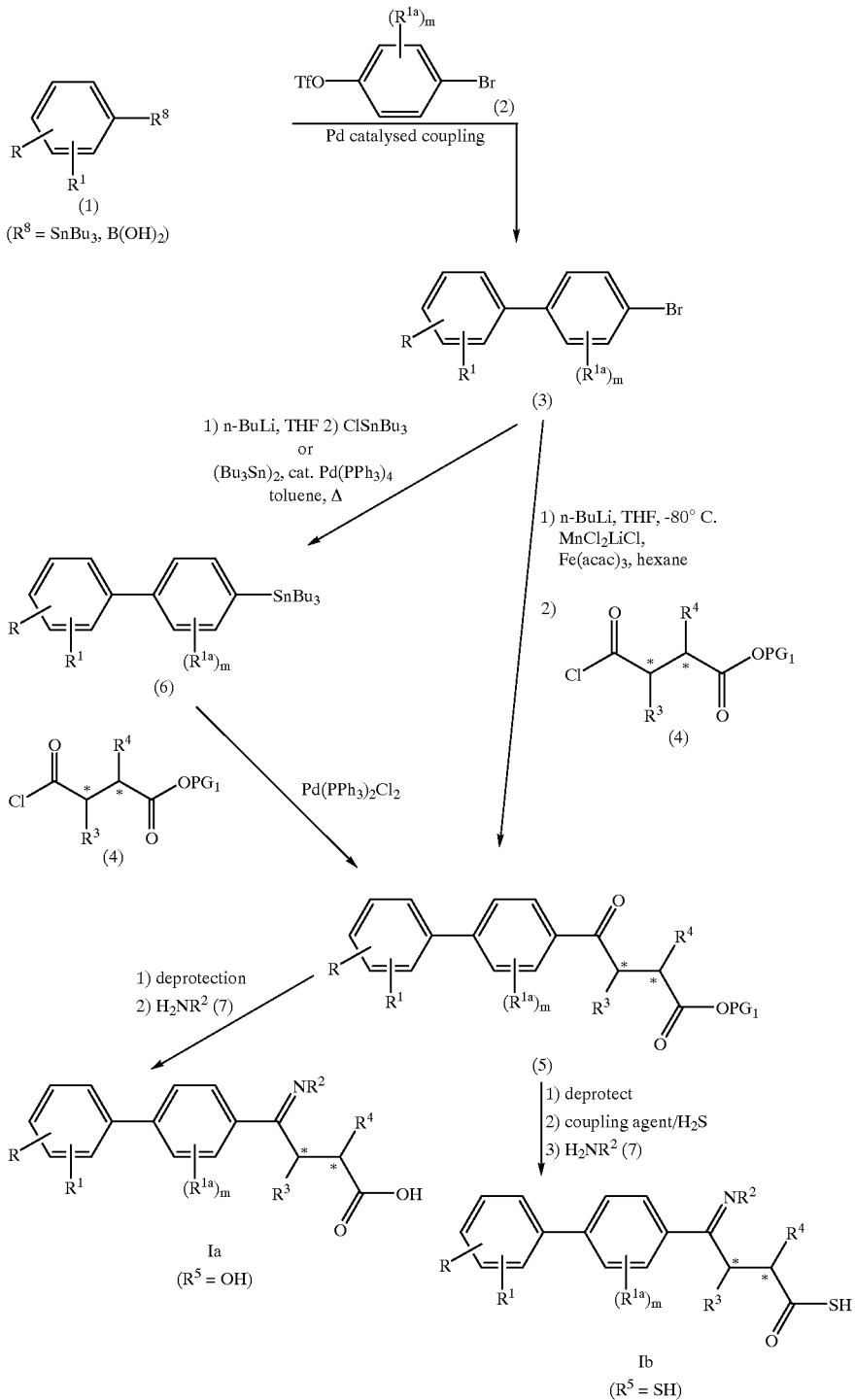

Route B:
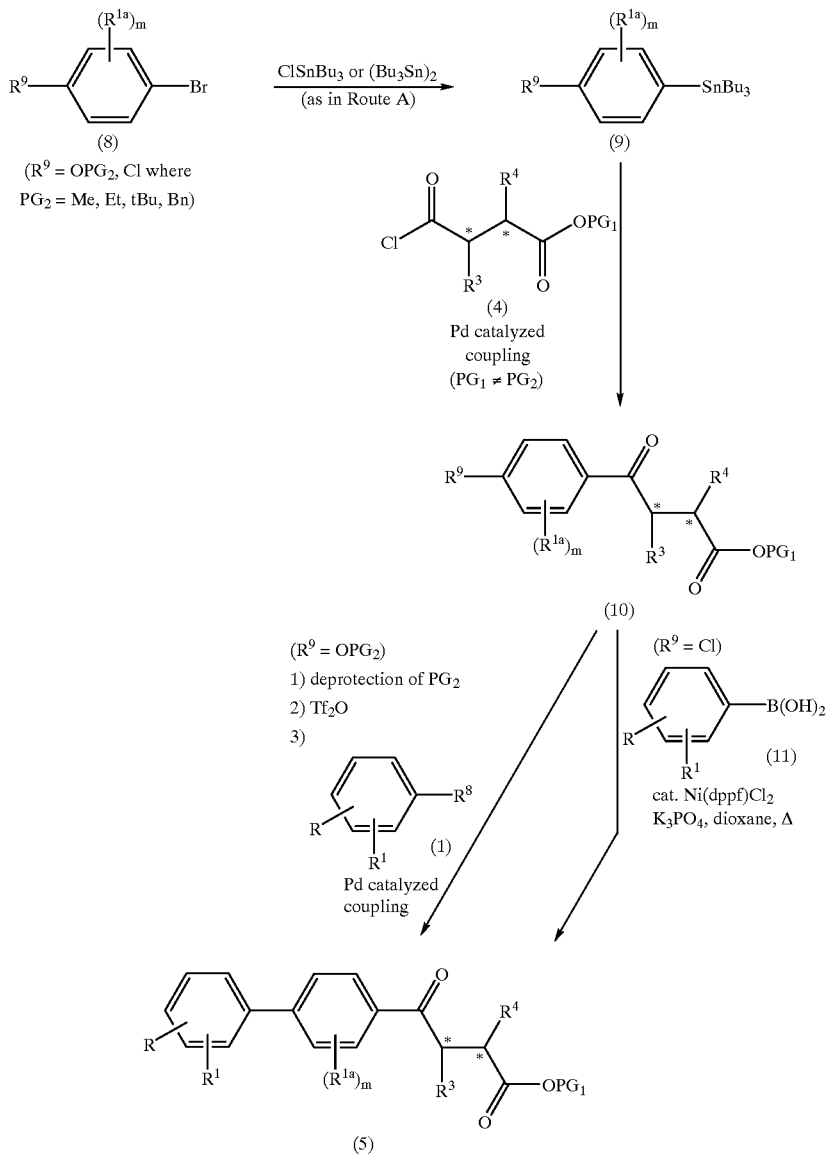

SCHEME 2
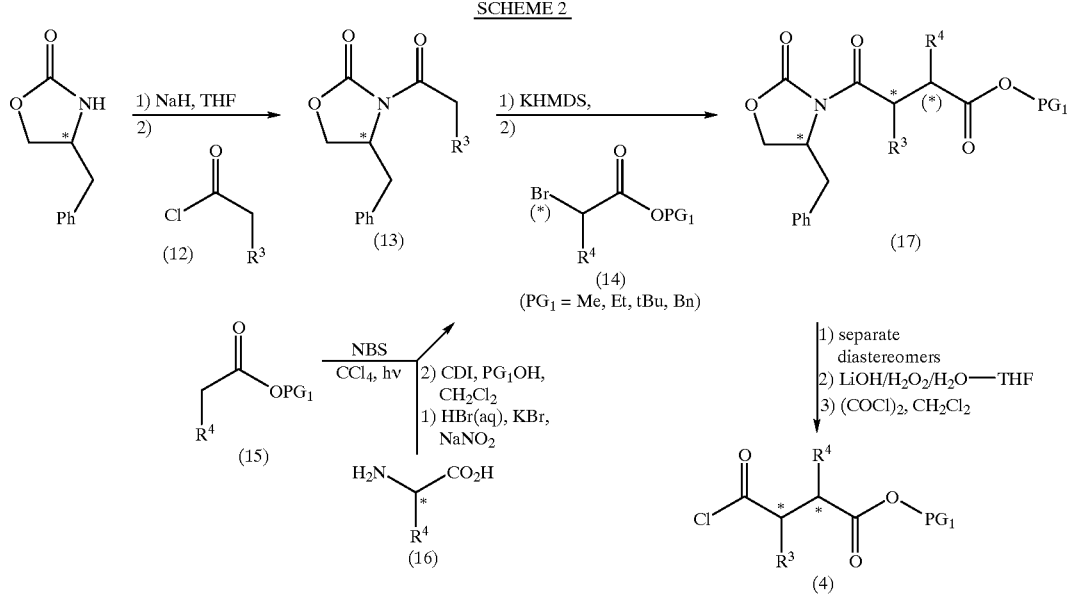
SCHEME 3
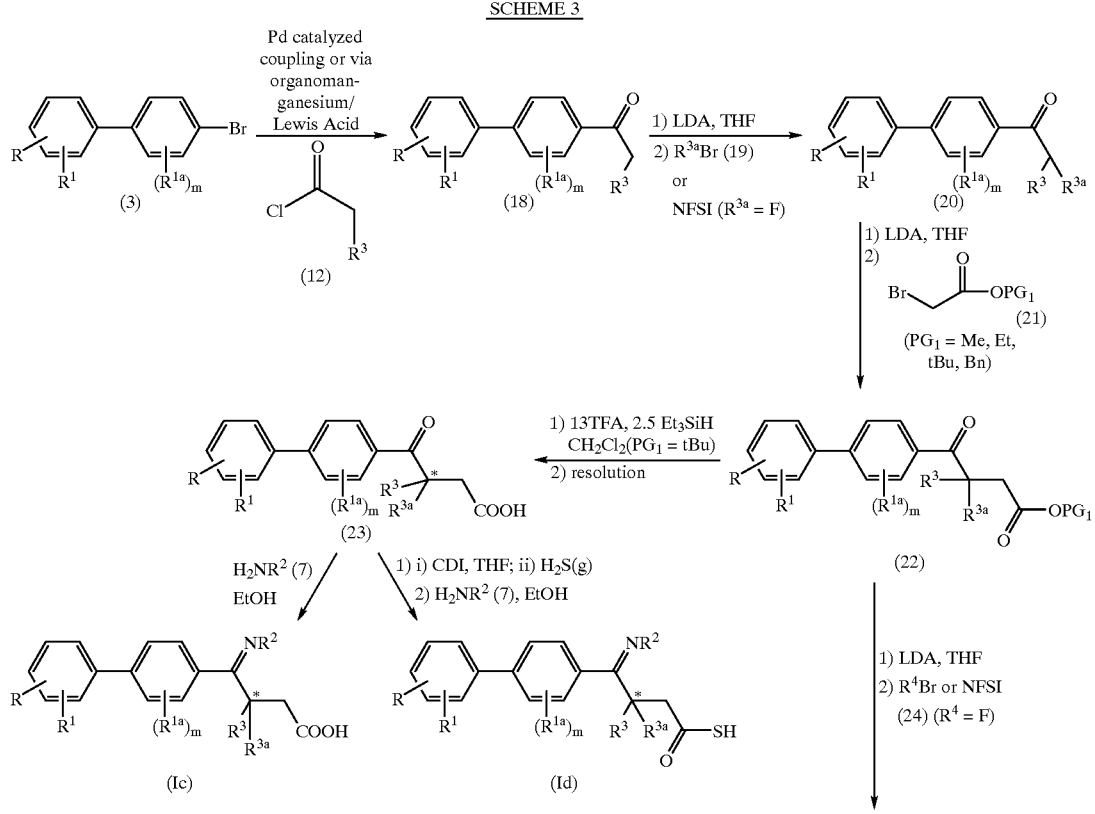

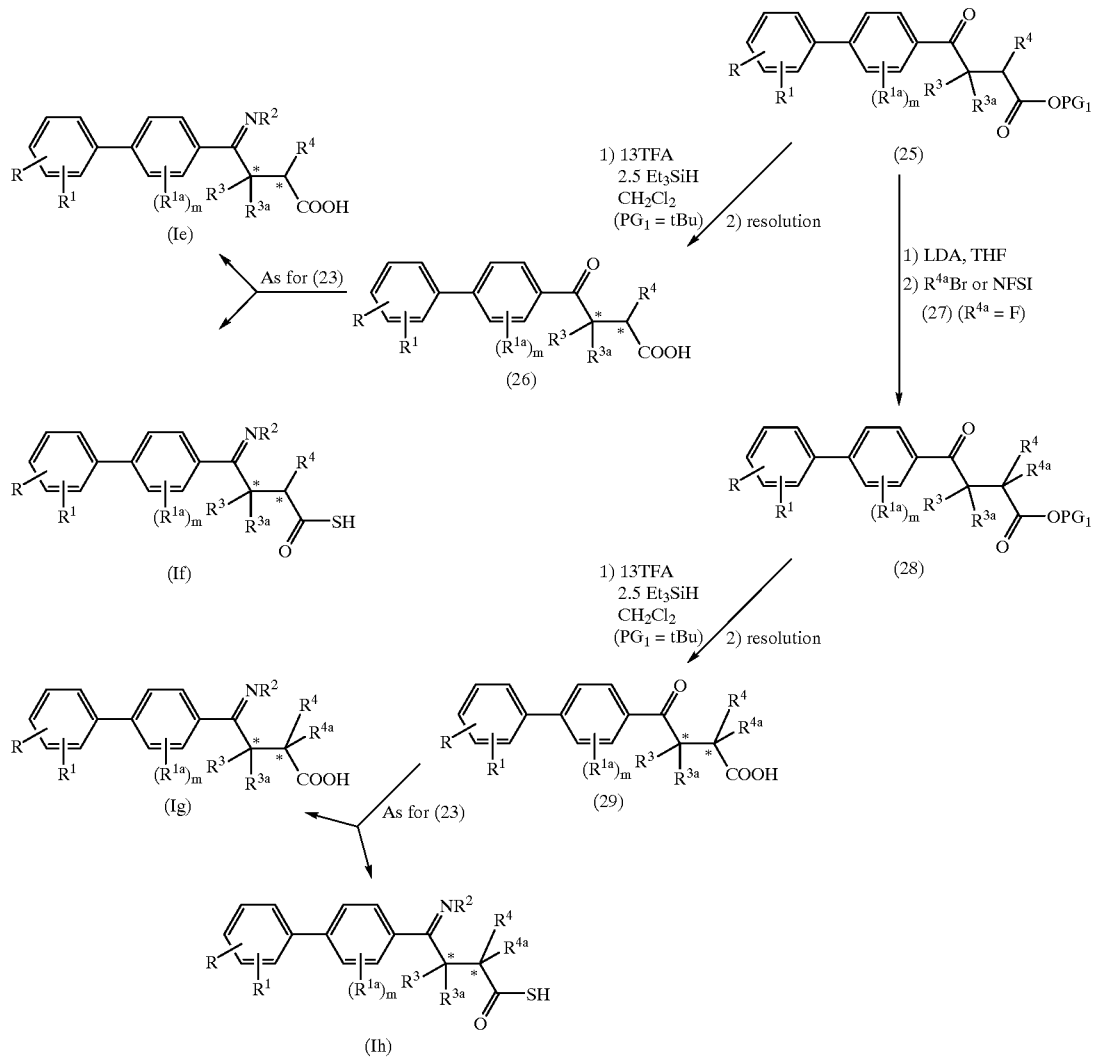

SCHEME 4
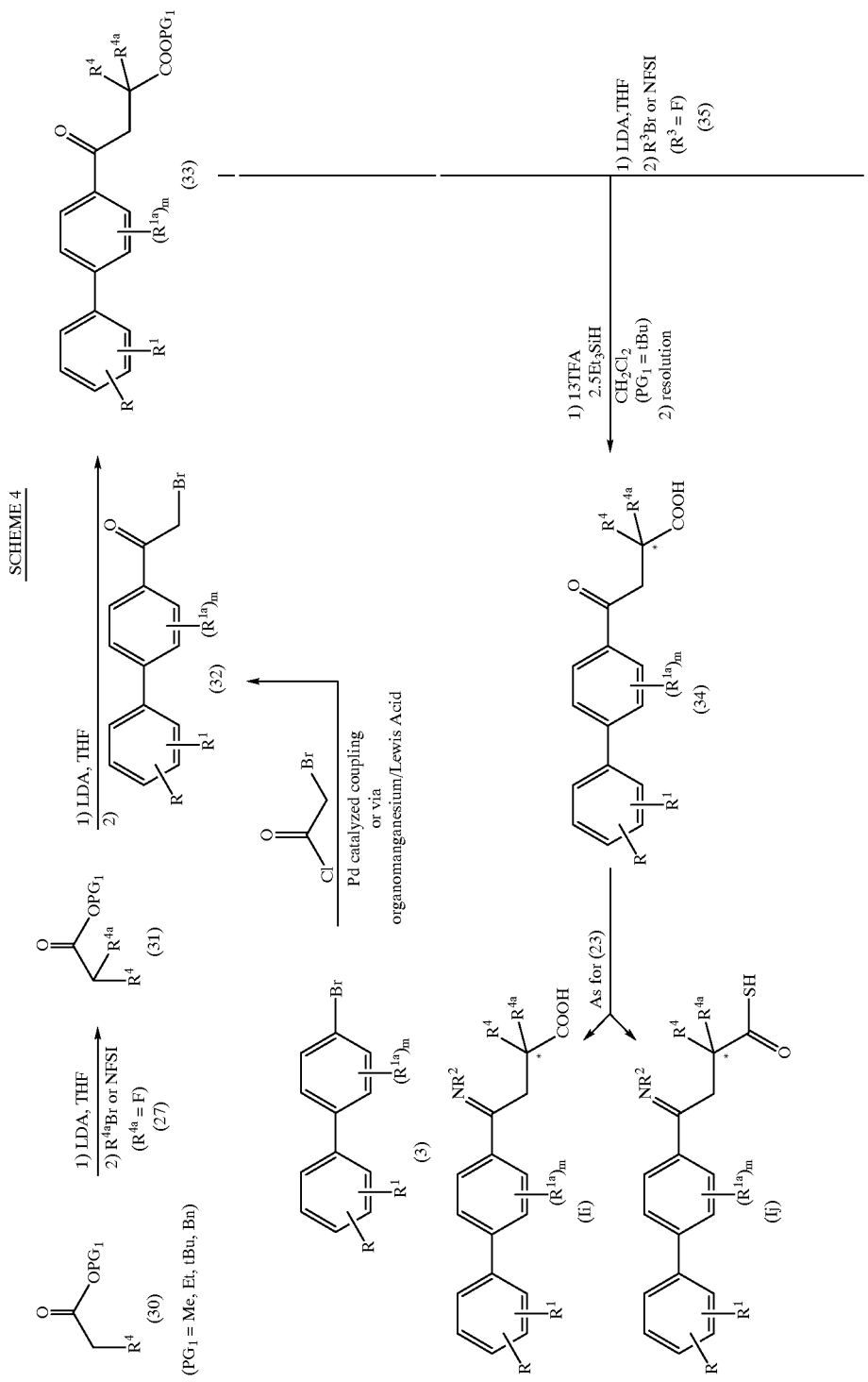

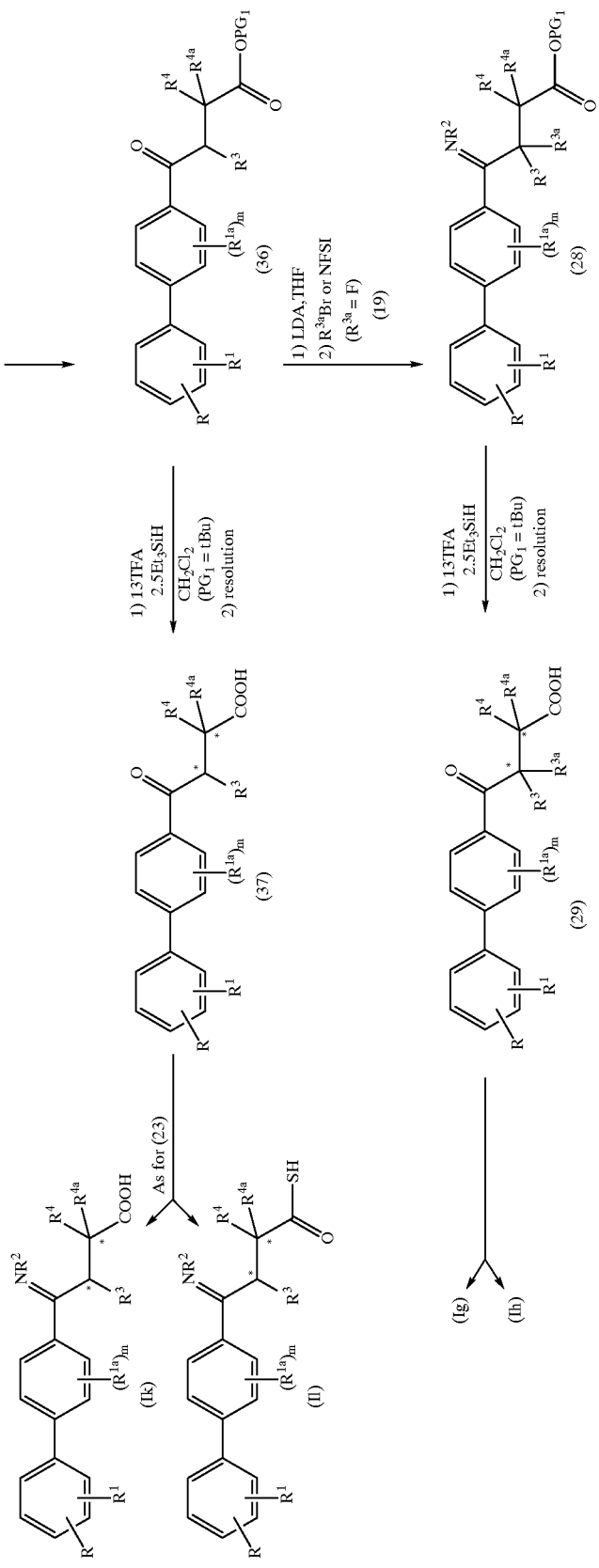

SCHEME 5
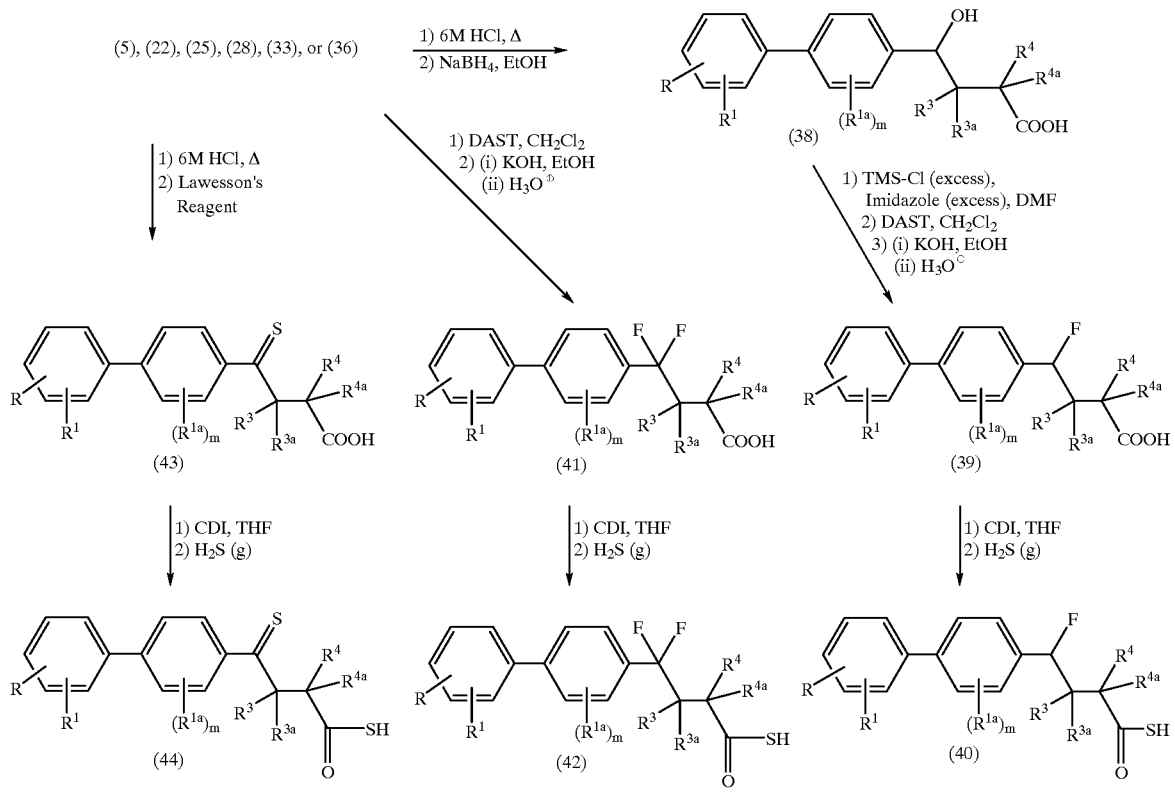
SCHEME 6
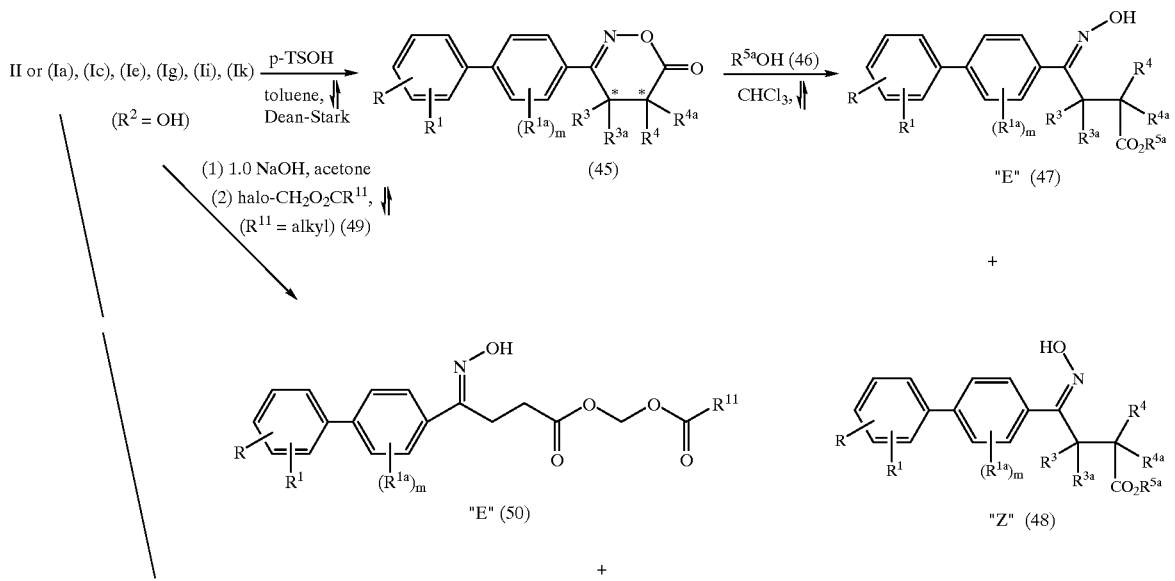

-continued

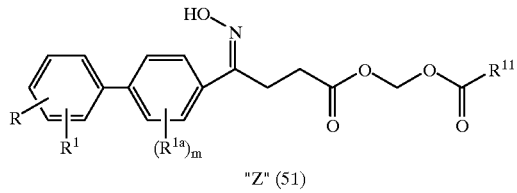

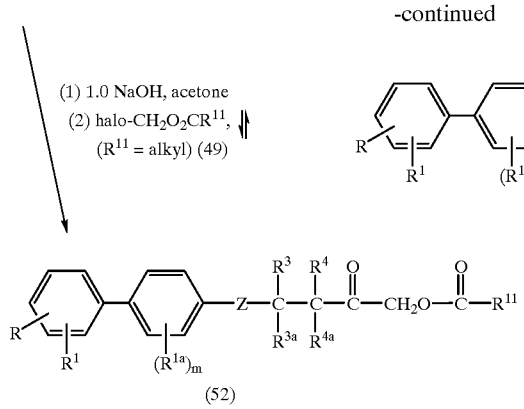

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or Formula II or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy the compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

What is claimed is:

1. A compound of Formula I

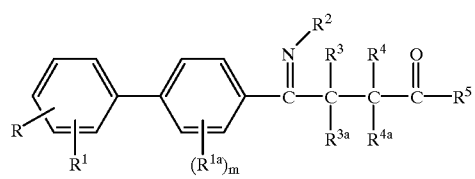

wherein R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
  alkyl,
  aryl,
  arylalkyl,
  heteroaryl, or
  cycloalkyl,

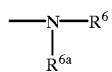

wherein $R^6$ and $R^{6a}$ are the same or different and are as defined above for $R^6$,

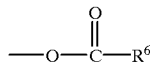

wherein $R^6$ is as defined above,

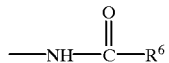

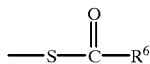

wherein $R^6$ is as defined above,
—$SR^6$ wherein $R^6$ is as defined above,

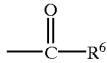

wherein $R^6$ is as defined above,
—$CH_2$—$OR^6$ wherein $R^6$ is as defined above,

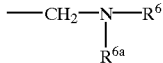

wherein $R^6$ and $R^{6a}$ are the same or different and are as defined above for $R^6$,

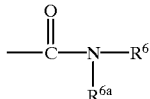

wherein $R^6$ and $R^{6a}$ are the same or different and are as defined above for $R^6$,

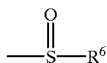

wherein $R^6$ is as defined above,

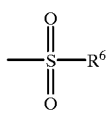

wherein $R^6$ is as defined above,
  cycloalkyl, or
  heteroaryl;
$R^{1a}$ is fluorine;
m is an integer of from 1 to 4;
$R^2$ is —$OR^6$ wherein $R^6$ is as defined above, or

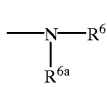

wherein $R^6$ and $R^{6a}$ are the same or different and are as defined above for $R^6$;
$R^3$, $R^{3a}$, $R^4$, and $R^{4a}$ are the same or different and are
  hydrogen,
  fluorine,
  alkyl,
  —$(CH_2)_n$-aryl wherein n is an integer from 1 to 6,
  —$(CH_2)_n$-heteroaryl wherein n is as defined above,
  —$(CH_2)_n$-cycloalkyl wherein n is as defined above,
  —$(CH_2)_p$—X—$(CH_2)_q$-aryl wherein X is O, S, SO, $SO_2$, or NH, and p and q are each zero or an integer of 1 to 6, and the sum of p+q is not greater than six, —(CH$_2$)$_p$—X—(CH$_2$)$_q$-heteroaryl wherein X, p, and q are as defined above, or —(CH$_2$)$_n$—R$^7$ wherein R$^7$ is N-phthalimido, N-2,3-naphthylimido, —OR$^6$ wherein R$^6$ is as defined above,

wherein R$^6$ and R$^{6a}$ are the same or different and as defined above for R$^6$, —SR$^6$ wherein R$^6$ is as defined above,

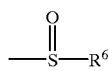

wherein R$^6$ is as defined above,

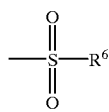

wherein R$^6$ is as defined above,

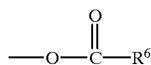

wherein R$^6$ is as defined above,

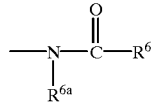

wherein R$^6$ and R$^{6a}$ are the same or different and are as defined above for R$^6$,

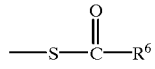

wherein R$^6$ is as defined above,

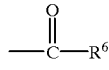

wherein R$^6$ is as defined above,

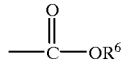

wherein R$^6$ is as defined above, or

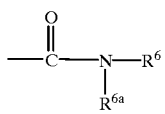

wherein R$^6$ and R$^{6a}$ are the same or different and are as defined above for R$^6$, and n is as defined above;

R$^5$ is OH, SH; or OR$^{5a}$ wherein R$^{5a}$ is alkyl, arylalkyl, cycloalkyl, or acyloxymethyl;

with the proviso that R$^3$, R$^{3a}$, R$^4$, and R$^{4a}$ are hydrogen or at least one of R$^3$, R$^{3a}$, R$^4$, or R$^{4a}$ is fluorine;

and corresponding isomers thereof; or a pharmaceutically acceptable salt thereof.

2. A compound according to claim 1 wherein R$^2$ is OR$^6$.

3. A compound according to claim 2 wherein R$^2$ is OCH$_3$.

4. A compound according to claim 3 wherein R$^2$ is OH; and R$^3$, R$^{3a}$, R$^4$, and R$^{4a}$ are hydrogen.

5. A compound according to claim 1 wherein R$^2$ is OH, and at least one of R$^3$, R$^{3a}$, R$^4$, and R$^{4a}$ is fluorine.

6. A compound selected from the group consisting of:

4-(2-Fluoro-biphenyl-4-yl)-4-hydroxyimino-butyric acid;

4-(3-Fluoro-biphenyl-4-yl)-4-hydroxyimino-butyric acid;

4-(4'-Chloro-2-fluoro-biphenyl-4-yl)-4-methoxyimino-butyric acid;

4-(4'-Chloro-3-fluoro-biphenyl-4-yl)-4-methoxyimino-butyric acid;

4-(4'-Chloro-2-fluoro-biphenyl 4-yl)-4-hydroxyimino-butyric acid;

4-(4'-Chloro-3-fluoro-biphenyl-4-yl)-4-hydroxyimino-butyric acid;

4-(4'-Chloro-2,3-difluoro-biphenyl-4-yl)-4-hydroxyimino-butyric acid;

4-(4'-Chloro-2,6-difluoro-biphenyl-4-yl)-4-hydroxyimino-butyric acid;

4-(4'-Chloro-3,5-difluoro-biphenyl-4-yl)-4-hydroxyimino-butyric acid;

4-(4'-Chloro-2,3,5-trifluoro-biphenyl-4-yl)4-hydroxyimino-butyric acid;

4-(4'-Chloro-2,3,6-trifluoro-biphenyl-4-yl)-4-hydroxyimino-butyric acid;

4-(4'-Chloro-2,3,5,6-tetrafluoro-biphenyl-4-yl)-4-hydroxyimino-butyric acid;

4-(4'-Bromo-2-fluoro-biphenyl-4-yl)-4-hydroxyimino-butyric acid;

4-(4'-Bromo-3-fluoro-biphenyl-4-yl)-4-hydroxyimino-butyric acid;

4-(4'-Chloro-2-fluoro-biphenyl-4-yl)-4-hydroxyimino-butyric acid;

4-(4'-Chloro-3-fluoro-biphenyl-4-yl)-4-hydroxyimino-butyric acid;

4-(2,4'-Difluoro-biphenyl-4-yl)-4-hydroxyimino-butyric acid;

4-(3,4'-Difluoro-biphenyl-4-yl)-4-hydroxyimino-butyric acid;

4-(2,3'-Difluoro-biphenyl-4-yl)-4-hydroxyimino-butyric acid;

4-(3,3'-Difluoro-biphenyl-4-yl)-4-hydroxyimino-butyric acid;

4-(2,2'-Difluoro-biphenyl-4-yl)-4-hydroxyimino-butyric acid;

4-(2',3-Difluoro-biphenyl-4-yl)-4-hydroxyimino-butyric acid;
4-(4'-Cyano-2-fluoro-biphenyl-4-yl)-4-hydroxyimino-butyric acid;
4-(4'-Cyano-3-fluoro-biphenyl-4-yl)-4-hydroxyimino-butyric acid;
4-(2-Fluoro-4'-methoxy-biphenyl-4-yl)-4-hydroxyimino-butyric acid;
4-(3-Fluoro-4'-methoxy-biphenyl-4-yl)-4-hydroxyimino-butyric acid;
4-(2-Fluoro-4'-methyl-biphenyl-4-yl)-4-hydroxyimino-butyric acid;
4-(3-Fluoro-4'-methyl-biphenyl-4-yl)-4-hydroxyimino-butyric acid;
4-(2-Fluoro-4'-hydroxy-biphenyl-4-yl)-4-hydroxyimino-butyric acid;
4-(3-Fluoro-4'-hydroxy-biphenyl-4-yl)-4-hydroxyimino-butyric acid;
4-(2-Fluoro-4'-methylsulfanyl-biphenyl-4-yl)-4-hydroxyimino-butyric acid;
4-(3-Fluoro-4'-methylsulfanyl-biphenyl-4-yl)-4-hydroxyimino-butyric acid;
4-(2-Fluoro-4'-trifluoromethyl-biphenyl-4-yl)-4-hydroxyimino-butyric acid;
4-(3-Fluoro-4'-trifluoromethyl-biphenyl-4-yl)-4-hydroxyimino-butyric acid;
(±)-4-(4'-Chloro-2-fluoro-biphenyl-4-yl)-2-fluoro-2-(3-phenylpropyl)-4-hydroxyimino-butyric acid;
(±)-4-(4'-Chloro-3-fluoro-biphenyl-4-yl)-2-fluoro-2-(3-phenylpropyl)-4-hydroxyimino-butyric acid;
(±)-4-(4'-Chloro-2-fluoro-biphenyl-4-yl)-2-fluoro-2-(2-phenylethyl)-4-hydroxyimino-butyric acid;
(±)-4-(4'-Chloro-3-fluoro-biphenyl-4-yl)-2-fluoro-2-(2-phenylethyl)-4-hydroxyimino-butyric acid;
(±)-4-(4'-Chloro-2-fluoro-biphenyl-4-yl)-2-fluoro-2-(3-phthalimidopropyl)-4-hydroxyimino-butyric acid;
(±)-4-(4'-Chloro-3-fluoro-biphenyl-4-yl)-2-fluoro-2-(3-phthalimidopropyl)-4-hydroxyimino-butyric acid;
(±)-4-(4'-Chloro-2-fluoro-biphenyl-4-yl)-2-fluoro-2-(1H-indol-3-yl)methyl-4-hydroxyimino-butyric acid;
(±)-4-(4'-Chloro-3-fluoro-biphenyl-4-yl)-2-fluoro-2-(1H-indol-3-yl)methyl-4-hydroxyimino-butyric acid;
(±)-4-(4'-Chloro-2-fluoro-biphenyl-4-yl)-2-(2,4-dioxo-1,5,5-trimethyl-imidazolidin-3-yl)methyl-2-fluoro-4-hydroxyimino-butyric acid; and
(±)-4-(4'-Chloro-3-fluoro-biphenyl-4-yl)-2-(2,4-dioxo-1,5,5-trimethyl-imidazolidin-3-yl)methyl-2-fluoro-4-hydroxyimino-butyric acid.

7. A compound selected from the group consisting of:
4-(2-Fluoro-biphenyl-4-yl)-4-hydroxyimino-butyric acid;
4-(3-Fluoro-biphenyl-4-yl)-4-hydroxyimino-butyric acid;
4-(4'-Chloro-2-fluoro-biphenyl-4-yl)-4-hydroxyimino-butyric acid;
and
4-(4'-Chloro-3-fluoro-biphenyl-4-yl)-4-hydroxyimino-butyric acid.

8. A method of inhibiting a matrix metalloproteinase comprising administering to a host suffering therefrom a therapeutically effective amount of a compound according to claim 1 in unit dosage form.

9. A method of inhibiting gelatinase A comprising administering to a host suffering therefrom a therapeutically effective amount of a compound according to claim 1 in unit dosage form.

10. A method of inhibiting stromelysin-1 comprising administering to a host suffering therefrom a therapeutically effective amount of a compound according to claim 1 in unit dosage form.

11. A method of treating atherosclerotic plaque rupture comprising administering to a host suffering therefrom a therapeutically effective amount of a compound according to claim 1 in unit dosage form.

12. A method of inhibiting aortic aneurism comprising administering to a host suffering therefrom a therapeutically effective amount of a compound according to claim 1 in unit dosage form.

13. A method of inhibiting heart failure comprising administering to a host suffering therefrom a therapeutically effective amount of a compound according to claim 1 in unit dosage form.

14. A method of treating restenosis comprising administering to a host suffering therefrom a therapeutically effective amount of a compound according to claim 1 in unit dosage form.

15. A method of controlling periodontal disease comprising administering to a host suffering therefrom a therapeutically effective amount of a compound according to claim 1 in unit dosage form.

16. A method of treating corneal ulceration comprising administering to a host suffering therefrom a therapeutically effective amount of a compound according to claim 1 in unit dosage form.

17. A method of treating burns comprising administering to a host suffering therefrom a therapeutically effective amount of a compound according to claim 1 in unit dosage form.

18. A method of treating decubital ulcers comprising administering to a host suffering therefrom a therapeutically effective amount of a compound according to claim 1 in unit dosage form.

19. A method of treatment for healing wounds comprising administering to a host suffering therefrom a therapeutically effective amount of a compound according to claim 1 in unit dosage form.

20. A method of treating cancer comprising administering to a host suffering therefrom a therapeutically effective amount of a compound according to claim 1 in unit dosage form.

21. A method of treating arthritis comprising administering to a host suffering therefrom a therapeutically effective amount of a compound according to claim 1 in unit dosage form.

22. A method of treating autoimmune or inflammatory disorders dependent upon tissue invasion by leukocytes comprising administering to a host suffering therefrom a therapeutically effective amount of a compound according to claim 1 in unit dosage form.

23. A method of treating multiple sclerosis comprising administering to a host suffering therefrom a therapeutically effective amount of a compound according to claim 1 in unit dosage form.

24. A method of treating inflammation and pain comprising administering to a host suffering therefrom a therapeutically effective amount of a compound according to claim 1 in unit dosage form.

25. A method of treating acute and chronic neurodegenerative disorders selected from the group consisting of: stroke, head trauma, spinal cord injury, Alzheimer's disease, amyotrophic lateral sclerosis, cerebral amyloid angiopathy, AIDS-associated CNS disorders, Parkinson's disease, Huntington's diseases, prion diseases, myasthenia gravis, and Duchenne's muscular dystrophy comprising administering to a host suffering therefrom a therapeutically effective amount of a compound according to claim 1 in unit dosage form.

26. A method of treating renal disease comprising administering to a host suffering therefrom a therapeutically effective amount of a compound according to claim 1 in unit dosage form.

27. A pharmaceutical composition comprising a compound according to claim 1 in admixture with a pharmaceutically acceptable excipient, diluent, or carrier.

28. A pharmaceutical composition comprising a therapeutically effective amount of a compound according to claim 1 in admixture with a pharmaceutically acceptable excipient, diluent, or carrier.

29. A method for preparing a compound having the Formula Ia

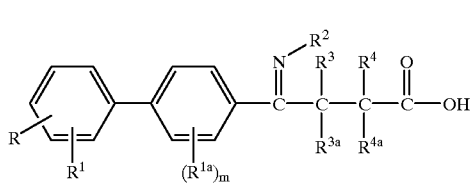

wherein R and $R^1$ are the same or different and are
hydrogen,
alkyl,
halogen,
nitro,
cyano,
trifluoromethyl,
$OCF_3$,
$OCF_2H$,
$OCH_2F$,
—$OR^6$ wherein $R^6$ is hydrogen,
  alkyl,
  aryl,
  arylalkyl,
  heteroaryl, or
  cycloalkyl,

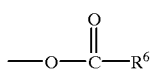

wherein $R^6$ and $R^{6a}$ are the same or different and are as defined above for $R^6$,

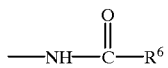

wherein $R^6$ is as defined above,

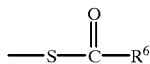

wherein $R^6$ is as defined above,

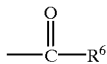

wherein $R^6$ is as defined above,
—$SR^6$ wherein $R^6$ is as defined above,

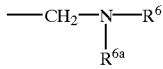

wherein $R^6$ is as defined above,
—$CH_2$—$OR^6$ wherein $R^6$ is as defined above,

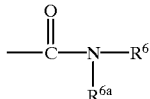

wherein $R^6$ and $R^{6a}$ are the same or different and are as defined above for $R^6$,

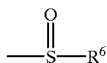

wherein $R^6$ and $R^{6a}$ are the same or different and are as defined above for $R^6$,

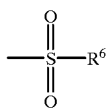

wherein $R^6$ is as defined above,

wherein $R^6$ is as defined above,
cycloalkyl, or
heteroaryl;
$R^{1a}$ is fluorine;
m is an integer from 1 to 4;
$R^2$ is —$OR^6$ wherein $R^6$ is as defined above, or wherein $R^6$ and $R^{6a}$ are the same or different and are as defined above for $R^6$;
$R^3$, $R^{3a}$, $R^4$, and $R^{4a}$ are the same or different and are
hydrogen,
fluorine,
alkyl,
—$(CH_2)_n$-aryl wherein n is an integer from 1 to 6,
—$(CH_2)_n$-heteroaryl wherein n is as defined above,
—$(CH_2)_n$-cycloalkyl wherein n is as defined above,
—$(CH_2)_p$—X—$(CH_2)_q$-aryl wherein X is O, S, SO, $SO_2$, or NH, and p and q are each zero or an integer of 1 to 6, and the sum of p+q is not greater than six, —$(CH_2)_p$—X—$(CH_2)_q$-heteroaryl wherein X, p, and q are as defined above, or —$(CH_2)_n$—$R^7$ wherein $R^7$ is N-phthalimido, N-2,3-naphthylimido, —$OR^6$ wherein $R^6$ is as defined above,

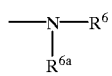

wherein $R^6$ and $R^{6a}$ are the same or different and are as defined above for $R^6$, —$SR^6$ wherein $R^6$ is as defined above,

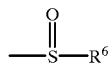

wherein $R^6$ is as defined above,

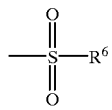

wherein $R^6$ is as defined above,

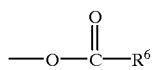

wherein $R^6$ is as defined above,

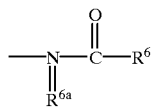

wherein $R^6$ and $R^{6a}$ are the same or different and are as defined above for $R^6$,

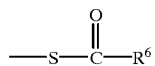

wherein $R^6$ is as defined above,

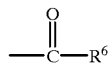

wherein $R^6$ is as defined above,

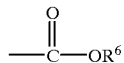

wherein $R^6$ is as defined above, or

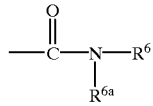

wherein $R^6$ and $R^{6a}$ are the same or different and are as defined above for $R^6$, and n is as defined above; with the proviso that $R^3$, $R^{3a}$, $R^4$, and $R^{4a}$ are hydrogen or at least one of $R^3$, $R^{3a}$, $R^4$, or $R^{4a}$ is fluorine; and corresponding isomers thereof, or a pharmaceutically acceptable salt thereof which comprises deprotection of a compound of Formula (5a)

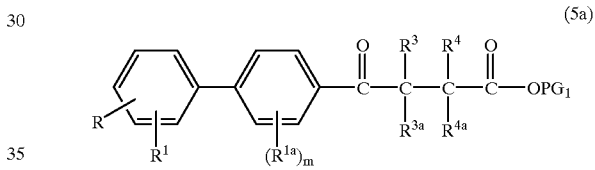

(5a)

wherein $PG_1$ is selected from the group consisting of methyl, ethyl, tert-butyl, and benzyl, and R, $R^1$, $R^{1a}$, $R^3$, $R^{3a}$, $R^4$, $R^{4a}$ and m are as defined above using standard methodology followed by condensation with a compound of Formula (7)

(7)

$H_2NR^2$ wherein $R^2$ is as defined above to give a compound of Formula Ia and if desired, converting a compound of Formula Ia to a corresponding pharmaceutically acceptable salt by conventional means and, if so desired, converting the corresponding pharmaceutically acceptable salt to a compound of Formula Ia by conventional means.

* * * * *

UNITED STATES PATENT AND TRADEMARK OFFICE
CERTIFICATE OF CORRECTION

PATENT NO.      : 6,169,103 B1
DATED           : January 2, 2001
INVENTOR(S)     : Purchase, Jr. et al.

It is certified that error appears in the above-identified patent and that said Letters Patent is hereby corrected as shown below:

Column 3,
Line 3, "16:417424)" should read -- 16:417-424) --
Line 12, "1969;81 :370-373)" should read -- 1969;81:370-373) --

Column 4,
Line 8, "1994;201 :94-101" should read -- 1994;201:94-101) --
Line 10, "GM600 1" should read -- GM6001 --

Column 6,
Line 23, "1992;41 :671-678)" should read -- 1992;41:671-678) --

Column 10,
Line 8, delete "-SR$^6$" before the word "wherein"

Column 17,
Line 62, "4 hydroxyimino" should read -- 4-hydroxyimino --

Column 21,
Line 53, "often" should read -- of ten --

Signed and Sealed this

Thirtieth Day of July, 2002

Attest:

JAMES E. ROGAN
Attesting Officer                Director of the United States Patent and Trademark Office